US010533174B2

(12) United States Patent
Iversen et al.

(10) Patent No.: US 10,533,174 B2
(45) Date of Patent: *Jan. 14, 2020

(54) SPLICE-REGION ANTISENSE COMPOSITION AND METHOD

(71) Applicant: Sarepta Therapeutics, Inc., Cambridge, MA (US)

(72) Inventors: Patrick L. Iversen, Corvallis, OR (US); Robert Hudziak, Blodgett, OR (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/723,966

(22) Filed: Oct. 3, 2017

(65) Prior Publication Data

US 2018/0237773 A1   Aug. 23, 2018

Related U.S. Application Data

(63) Continuation of application No. 15/205,722, filed on Jul. 8, 2016, now abandoned, which is a continuation of application No. 14/535,098, filed on Nov. 6, 2014, now Pat. No. 9,416,361, which is a continuation of application No. 13/859,518, filed on Apr. 9, 2013, now Pat. No. 8,895,722, which is a continuation of application No. 13/219,409, filed on Aug. 26, 2011, now Pat. No. 8,436,163, which is a continuation of application No. 10/893,086, filed on Jul. 16, 2004, now abandoned, which is a continuation of application No. 09/848,868, filed on May 4, 2001, now Pat. No. 6,784,291.

(60) Provisional application No. 60/202,376, filed on May 4, 2000.

(51) Int. Cl.
   *C07H 21/02*   (2006.01)
   *C07H 21/04*   (2006.01)
   *C12N 15/113*  (2010.01)

(52) U.S. Cl.
   CPC ........ *C12N 15/113* (2013.01); *C12N 2310/11* (2013.01); *C12N 2310/3233* (2013.01); *C12N 2320/33* (2013.01)

(58) Field of Classification Search
   CPC .......................... C12N 15/111; C12N 15/113
   See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton |
| 5,217,866 A | 6/1993 | Summerton et al. |
| 5,506,337 A | 4/1996 | Summerton et al. |
| 5,521,063 A | 5/1996 | Summerton et al. |
| 5,627,274 A | 5/1997 | Kole et al. |
| 5,665,593 A | 9/1997 | Kole et al. |
| 5,698,685 A | 12/1997 | Summerton et al. |
| 5,776,905 A | 7/1998 | Gibbons et al. |
| 5,811,537 A | 9/1998 | Friesen |
| 5,830,670 A | 11/1998 | de la Monte et al. |
| 5,858,684 A | 1/1999 | Nemeth et al. |
| 5,892,023 A | 4/1999 | Pirotzky et al. |
| 5,914,396 A | 6/1999 | Cook et al. |
| 5,916,808 A | 6/1999 | Kole et al. |
| 5,976,879 A | 11/1999 | Kole et al. |
| 5,998,148 A | 12/1999 | Bennett et al. |
| 6,043,091 A | 3/2000 | Monia et al. |
| 6,046,319 A | 4/2000 | Power et al. |
| 6,060,456 A | 5/2000 | Arnold, Jr. et al. |
| 6,103,466 A | 8/2000 | Grobet et al. |
| 6,133,242 A | 10/2000 | Zalewski et al. |
| 6,133,246 A | 10/2000 | McKay et al. |
| 6,171,798 B1 | 1/2001 | Levine et al. |
| 6,172,216 B1 | 1/2001 | Bennett et al. |
| 6,183,964 B1 | 2/2001 | Boeke et al. |
| 6,210,892 B1 | 4/2001 | Bennett et al. |
| 6,214,986 B1 | 4/2001 | Bennett et al. |
| 6,228,579 B1 | 5/2001 | Zyskind et al. |
| 6,239,265 B1 | 5/2001 | Cook |

(Continued)

FOREIGN PATENT DOCUMENTS

| | | |
|---|---|---|
| AU | 2003284638 A8 | 6/2004 |
| AU | 780517 B2 | 3/2005 |

(Continued)

OTHER PUBLICATIONS

Aartsma-Rus et al. (2002) "Targeted exon skipping as a potential gene correction therapy for Duchenne muscular dystrophy," Neuromuscular Disorders 12(Suppl):S71-S77.
Aartsma-Rus et al. (2003) "Therapeutic antisense-induced exon skipping in cultured muscle cells from six different DMD patients," Human Molecular Genetics 12(8):907-914.
Aartsma-Rus et al. (2004) "Antisense-Induced Multiexon Skipping for Duchenne Muscular Dystrophy Makes More Sense," American Journal of Human Genetics 74:83-92.

(Continued)

*Primary Examiner* — Amy H Bowman
(74) *Attorney, Agent, or Firm* — Brian C. Trinque; Alan W. Steele; Lathrop Gage LLP

(57) ABSTRACT

Antisense compositions targeted against an mRNA sequence coding for a selected protein, at a region having its 5' end from 1 to about 25 base pairs downstream of a normal splice acceptor junction in the preprocessed mRNA, are disclosed. The antisense compound is RNase-inactive, and is preferably a phosphorodiamidate-linked morpholino oligonucleotide. Such targeting is effective to inhibit natural mRNA splice processing, produce splice variant mRNAs, and inhibit normal expression of the protein.

13 Claims, 2 Drawing Sheets
Specification includes a Sequence Listing.

(56) References Cited

U.S. PATENT DOCUMENTS

| | | | |
|---|---|---|---|
| 6,365,351 | B1 | 4/2002 | Iversen |
| 6,495,663 | B1 | 12/2002 | Rothbard et al. |
| 6,653,467 | B1 | 11/2003 | Matsuo et al. |
| 6,677,153 | B2 | 1/2004 | Iversen |
| 6,727,355 | B2 | 4/2004 | Matsuo et al. |
| 6,784,291 | B2 | 8/2004 | Iversen et al. |
| 6,828,105 | B2 | 12/2004 | Stein et al. |
| 6,841,542 | B2 | 1/2005 | Bartelmez et al. |
| 7,049,431 | B2 | 5/2006 | Iversen |
| 7,094,765 | B1 | 8/2006 | Iversen et al. |
| 7,148,204 | B2 | 12/2006 | Bennett et al. |
| 8,067,569 | B2 | 11/2011 | Iversen et al. |
| 8,436,163 | B2 | 5/2013 | Iversen et al. |
| 8,895,722 | B2 | 11/2014 | Iversen et al. |
| 9,416,361 | B2 * | 8/2016 | Iversen .............. C07F 9/65583 |
| 2001/0007025 | A1 | 7/2001 | Bennett et al. |
| 2001/0056077 | A1 | 12/2001 | Matsuo |
| 2002/0049173 | A1 | 4/2002 | Bennett et al. |
| 2002/0055481 | A1 | 5/2002 | Matsuo et al. |
| 2003/0166588 | A1 | 9/2003 | Iversen et al. |
| 2003/0224353 | A1 | 12/2003 | Stein et al. |
| 2004/0242528 | A1 | 12/2004 | Hagstrom et al. |
| 2004/0266720 | A1 | 12/2004 | Iversen et al. |
| 2005/0202531 | A1 | 9/2005 | Toporik |
| 2006/0287268 | A1 | 12/2006 | Iversen et al. |
| 2007/0105807 | A1 | 5/2007 | Sazani et al. |
| 2007/0111962 | A1 | 5/2007 | Mourich et al. |
| 2007/0122821 | A1 | 5/2007 | Iversen et al. |
| 2007/0155685 | A1 | 7/2007 | Schilingensiepen et al. |
| 2007/0249538 | A1 | 10/2007 | Sazani et al. |
| 2008/0200409 | A1 | 8/2008 | Wilson et al. |
| 2009/0105139 | A1 | 4/2009 | Kole et al. |
| 2009/0110689 | A1 | 4/2009 | Mourich et al. |
| 2009/0246221 | A1 | 10/2009 | Mourich et al. |

FOREIGN PATENT DOCUMENTS

| | | | |
|---|---|---|---|
| CA | 2248762 | A1 | 4/1999 |
| CA | 2400573 | A1 | 10/2001 |
| EP | 1 054 058 | A1 | 11/2000 |
| EP | 1 160 318 | A1 | 10/2001 |
| EP | 1 507 005 | A2 | 2/2005 |
| EP | 1 544 297 | A2 | 6/2005 |
| WO | 1993/001286 | A2 | 1/1993 |
| WO | 1994/006476 | A1 | 3/1994 |
| WO | 1994/026887 | A1 | 11/1994 |
| WO | 1997/034638 | A1 | 9/1997 |
| WO | 2000/020432 | A1 | 4/2000 |
| WO | 2000/044897 | A1 | 8/2000 |
| WO | 2000/053624 | A1 | 9/2000 |
| WO | 2000/058512 | A1 | 10/2000 |
| WO | 2001/072765 | A1 | 10/2001 |
| WO | 2001/083740 | A2 | 11/2001 |
| WO | 2002/008893 | A1 | 1/2002 |
| WO | 2002/024906 | A1 | 3/2002 |
| WO | 2002/074989 | A2 | 9/2002 |
| WO | 2003/070897 | A2 | 8/2003 |
| WO | 2004/048570 | A1 | 6/2004 |
| WO | 2004/083432 | A1 | 9/2004 |
| WO | 2006/000057 | A1 | 1/2006 |
| WO | 2006/047683 | A2 | 5/2006 |
| WO | 2006/086667 | A2 | 8/2006 |
| WO | 2006/108241 | A1 | 10/2006 |
| WO | 2007/056466 | A2 | 5/2007 |
| WO | 2007/058894 | A2 | 5/2007 |
| WO | 2008/036127 | A2 | 3/2008 |
| WO | 2008/051306 | A1 | 5/2008 |
| WO | 2008/131807 | A2 | 11/2008 |
| WO | 2008/153933 | A2 | 12/2008 |
| WO | 2009/086469 | A2 | 7/2009 |
| WO | 2010/054267 | A1 | 5/2010 |

OTHER PUBLICATIONS

Abood et al. (1994) "Molecular Cloning and Expression of a 6-Opioid Receptor From Rat Brain," J. Neurosci. Res. 37:714-719.
Agrawal et al. (1988) "Oligodeoxynucleoside as inhibitors of human immunodeficiency phosphoramidates and phosphorothioates virus," Proc. Natl. Acad. Sci. USA. 85(19):7079-7083.
Agrawal et al. (2000) "Antisense therapeutics: is it as simple as complementary base recognition?" Molecular Medicine Today 6:72-81.
Alter et al. (2006) "Systemic delivery of morpholino oligonucleotide restores dystrophin expression bodywide and improves dystrophic pathology," Nature Medicine 12(2):175-177.
Amarante-Mendes et al. (1998) "Bcl-2-independent Bcr-Abl-mediated resistance to apoptosis: protection is correlated with up regulation of Bcl-x," Oncogene 16:1383-1390.
Bailey et al. (1998) "Cationic oligonucleotides can mediate specific inhibition of gene expression in Xenopus oocytes," Nucleic Acids Res. 26(21): 4860-7.
Barawkar et al. (1998) "Synthesis, biophysical properties, and nuclease resistance properties of mixed backbone oligodeoxynucleotides containing cationic internucleoside guanidinium linkages: deoxynucleic guanidine/DNA chimeras," Proc Natl Acad Sci USA. 95(19): 11047-52.
Braasch et al. (2002) "Novel Antisense and Peptide Nucleic Acid Strategies for Controlling Gene Expression," Biochemistry 41(4):4503-4510.
Branch (1998) "A good antisense molecule is hard to find," TIBS (2):45-50.
Chirila et al. (2002) "The use of synthetic polymers for delivery of therapeutic antisense oligodeoxynucleotides," Biomaterials, 23(2): 321-342.
Condon et al. (1996) "Altered mRNA Splicing and Inhibition of Human E-selectin Expression by an Antisense Oligonucleotide in Human Umbilical Vein Endothelial Cells," J. Biol. Chem. 271(48):30398-30403.
Brooke (1999) Antisense Drug Technology: Principles, Strategies, and Applications. Marcel Dekker. New York, New York. pp. 1-50.
Brooke (2001) "Basic Principles of Antisense Technology," Ch. 1 In; Antisense Drug Technology. Springer-Verlag. pp. 1-28.
Daum et al. (1992) "Antisense Oligodeoxynucleotide: Inhibitor of Splicing of mRNA of Human Immunodeficiency Virus," Intervirology 33:65-75.
De Angelis et al. (2002) "Chimeric snRNA molecules carrying antisense sequences against the splice junctions of exon 51 of the dystrophin pre-mRNA induce exon skipping and restoration of a dystrophin synthesis in A 48-50 DMD cells," Proc Natl Acad Sci USA 99(14):9456-9461.
Dominiski et al. (1994) "Identification and Characterization by Antisense Oligonucleotides of Exon and Intron Sequences Required for Splicing," Mol. Cell Biol. 14(11):7445-7454.
Dominski et al. (1993) "Restoration of correct splicing in thalassemic pre-mRNA by antisense oligonucleotides," Proc Natl Acad Sci USA 90:8673-8677.
Dominski et al. (1994) "Identification of Exon Sequences Involved in Splice Site Selection," The Journal of Biological chemistry 269(38): 23590-23596.
Draper et al. (2001) "Inhibition of Zebrafish fgf8 Pre-mRNA Splicing With Morpholino Oligos: A Quantifiable Method for Gene Knockdown," Genesis 30(3): 154-156.
Dunckley et al. (1995) "Modification of splicing in the dystrophin gene in cultured Mdx muscle cells by antisense oligoribonucleotides," Human Molecular Genetics 5(1):1083-1090.
Errington et al. (2003) "Target selection for antisense oligonucleotide induced exon skipping in the dystrophin gene," J. Gene Medicine 5(6):518-527.
Furdon et al. (1989) "Inhibition of in vitro pre-mRNA splicing by antisense deoxyoligonucleotide analogues," Journal of Cellular Biochemistry 13D: Abstract.
Gerwirtz et al. (1998) "Nucleic Acid Therapeutics: State of the Art and Future Prospects," Blood 92(3):712-736.
Gilbert et al. (2001) "Sieve analysis: methods for assessing from vaccine trial data how vaccine efficacy varies with genotypic and phenotypic pathogen variation," Journal of Clinical Epidemiology 54(1):68-85.

(56) References Cited

OTHER PUBLICATIONS

Giles et al. (1999) "Antisense Morpholino Oligonucleotide Analog Induces Misspicing of C-myc mRNA," Antisense & Nucleic Acid Drug Development 9:213-220.
Gonzalez-Cadavid et al. (1998) "Organization of the human myostatin gene and expression in healthy men and HIV-Infected men with muscle wasting," PNAS 95:14938-14943.
Green et al. (2000) "Antisense Oligonucleotides: An Evolving Technology for the Modulation of Gene Expression in Human Disease," J Am. Coil. Surg. 1911):93-105.
Harel-Bellan et al. (1998) "Specific Inhibition of c-myc Protein Biosynthesis using an Antisense Synthetic Deoxy-Oligonucleotide in Human T Lymphocytes," The Journal of Immunology 140(7):2431-2435.
Heemskerk et al. (2009) "In vivo comparison of 2'-0-methyl phosphorothioate and morpholino antisense oligonucleotides for Duchenne muscular dystrophy exon skipping," The Journal of Gene Medicine 11:257-266.
Hodges et al. (1995) "Inhibition of Splicing of Wild-Type and Mutated Luciferase-Adenovirus Pre-mRNAs by Antisense Oligo-nucleotides," Molecular Pharmacology 48:905-918.
Hudziak et al. (1996) "Resistance of morpholino phosphorodiamidate oligomers to enzymatic degradation," Antisense Nucleic Acid Drug Dev. 6(4):267-272.
Hudziak et al. (2000) "Antiproliferative Effects of Steric Blocking Phosphorodiamidate Morpholino Antisense Agents Directed against c-myc," Antisense & Nucleic Acid Drug Development 10:163-176.
International Search Report corresponding to International Patent Application No. PCT/EP2007/061211, dated Dec. 18, 2008.
International Search Report corresponding to International Patent Application No. PCT/US1994/005181, dated Oct. 7, 1994.
International Search Report corresponding to International Patent Application No. PCT/US1999/022448, dated Dec. 23, 1999.
International Search Report corresponding to International Patent Application No. PCT/US2001/014410, dated Mar. 3, 2002.
International Search Report corresponding to International Patent Application No. PCT/US2006/004797, dated Dec. 15, 2006.
International Search Report corresponding to International Patent Application No. PCT/US2006/043507, dated May 23, 2007.
International Search Report corresponding to International Patent Application No. PCT/US2006/043651, dated Jun. 27, 2007.
International Search Report corresponding to International Patent Application No. PCT/US2007/010556, dated Mar. 13, 2008.
International Search Report corresponding to International Patent Application No. PCT/US2007/011435, dated Sep. 29, 2008.
International Search Report corresponding to International Patent Application No. PCT/US2008/088339, dated Jun. 4, 2009.
Ito et al. (2001) "Purine-rich exon sequences are not necessarily splicing enhancer sequence in the dystrophin gene," Kobe J. Med. Sci. 47:193-202.
Jen et al. (2000) "Suppression of Gene Expression by Targeted Disruption of Messenger RNA: Available Options and Current Strategies," Stem Cells 18:307-319.
Kean et al. (1995) "Inhibition of Herpes Simplex Virus Replication by Antisense Oligo-2'-0-methylribonucleoside Methylphosphonates," Biochemistry 34(45):14617-14621.
Kobayashi et al. (1995) "Growth inhibition of gastrointestinal cancer by antisense oligonucleotides," Osaka Daigaku Igaku Zasshi 47(6-12): 407-415.—with English machine translation.
Kole et al. (1991) "Pre-mRNA splicing as a target for antisense oligonucleotides," Advanced Drug Delivery Reviews 6:271-286.
U.S. Appl. No. 15/205,722, filed Jul. 8, 2016, Patrick L. Iversen.
Kole et al. (2004) "Modification of Alternative Splicing by Anti-sense Therapeutics," Oligonucleotides 14:65-74.
Lainez et al. (2004) "Identification and characterization of a novel spliced variant that encodes human soluble tumor necrosis factor receptor 2," International Immunology 16(1):169-177.
Linkletter et al. (2000) "Solid-Phase Synthesis of Positively Charged Deoxynucleic Guanidine (DNG) Modified Oligonucleotides Containing Neutral Urea Linkages: Effect of Charge Deletions on Binding and Fidelity," Bioorg. Med. Chem. 8(11):1893-1901.
McClorey et al. (2005) "Splicing intervention for Duchenne muscular dystrophy," Curr. Opin. Pharm. 5(5):529-534.
McClorey et al. (2006) "Antisense oligonucleotide-induced exon skipping restores dystrophin expression in vitro in a canine model of DMD," Gene Therapy 13(19):1373-1381.
Micklefield (2001) "Backbone modification of nucleic acids: synthesis, structure and therapeutic applications." Curr. Med. Chem. 8(10):1157-79.
Moulds et al. (1995) "Site and Mechanism of Antisense Inhibition by C-5 Propyne Oligonucleotides", Biochemistry 34(15):5044-5053.
Moulton et al. (2004) "Cellular Uptake of Antisense Morpholino Oligomers Conjugated to Arginine-Rich Peptides," Bioconjugate Chemistry 15:290-299.
Munroe (1988) "Antisense RNA inhibits splicing of pre-mRNA in vitro," EMBO 7:2523-2532.
Negri et al. (1999) "Differential Knockdown of 6-Opioid Receptor Subtypes in the Rat Brain by Antisense Oligodeoxynucleotides Targeting mRNA," Antisense & Nucleic Acid Drug Development 9:203-211.
Negri et al. (1999) "Effects of antisense oligonucleotides on brain delta-opioid receptor density and on SNC80-induced locomotor stimulation and colonic transit inhibition in rats," Br J Pharmacol 128:1554-1560.
Nelson et al. (2005) "Arginine-rich peptide conjugation to morpholino oligomers: effects on antisense activity and specificity," Bioconjug. Chem. 16(4): 959-66.
Palu et al. (1999) "In pursuit of new developments for gene therapy of human diseases," J Biotechnol. 68(1):1-13.
Roberts et al. (2006) "Efficient and Persistent Splice Switching by Systemically Delivered LNA Oligonucleotides in Mice," Molecular Therapy 14(4):471-475.
Rossi et al. (1997) "Antisense mapping DOR-1 in mice: further support for 6 receptor subtypes," Brain Res. 753:176-179.
Sazani et al. (2003) "Therapeutic potential of antisense oligonucle-otides as modulators of alternative splicing," Journal of Clinical Investigation 112(4):481-486.
Schmajuk et al. (1999) "Antisense Oligonucleotides with Different Backbones. Modification of splicing pathways and efficacy of uptake," J. Biol. Chem. 274:21783-21789.
Siwkowski et al. (2004) "Identification and functional validation of PNAs the inhibit murine CD40 expression by redirection of splicing," Nucleic Acids Research 32(9):2695-2706.
Summerton (1999) "Morpholino antisense oligomers: the case for an RNase H-independent structural type," . Biochimica Biophysica Acta 1489:141-158.
Summerton et al. (1997) "Morpholino and Phosphorothioate Antisense Oligomers Compared in Cell-Free and In-Cell Systems," Antisense & Nucleic Acid Drug Development 7:63-70.
Summerton et al. (1997) "Morpholino Antisense Oligomers: Design, Preparation, and Properties," Antisense & Nucleic Acid Drug Development 7:187-195.
Tamm et al. (2001) "Antisense therapy in oncology: new hope for an old idea?" The Lancet 358:489-497.
Taylor et al. (1999) "Induction of endogenous Bc1-xS through the control of Bcl-x pre-mRNA splicing by antisense oligonucleotides," Nature Biotechnology. 17:1097-1100 and 1064-1065.
Thornton et al. (2000) "From structure to function: approaches and limitations," Nat Struct Biol. 7(Suppl):991-4.
Volloch et al. (1991) "Inhibition of Pre-mRNA Splicing by Antisense RNA In Vitro: Effect of RNA Containing Sequences Complementary to Exons," Biochemical and Biophysical Research Communications 179(3):1593-1599.
Wengel et al. (1999) "Lna (Locked Nucleic Acid)," Nucleosides & Nucleotides 18(6-7):1365-1370.
Zhuang et al. (1989) "A compensatory base change in human U2 snRNA can suppress a branch site mutation," Gene Development 3(10):1545-1552.

(56) References Cited

OTHER PUBLICATIONS

Zollinger et al. (1991) "Meningococcal vaccines—present and future," Transactions of Royal Soc of Tropical Medicine and Hygiene. 85(Supp.1):37-43.

* cited by examiner

SPLICE-REGION ANTISENSE COMPOSITION AND METHOD

CROSS-REFERENCE TO RELATED APPLICATIONS

This application is a continuation of U.S. patent application Ser. No. 15/205,722, filed Jul. 8, 2016, which is a continuation of U.S. patent application Ser. No. 14/535,098, filed Nov. 6, 2014, now U.S. Pat. No. 9,416,361, which is a continuation of U.S. patent application Ser. No. 13/859,518, filed Apr. 9, 2013, now U.S. Pat. No. 8,895,722, which is a continuation of U.S. patent application Ser. No. 13/219,409, filed Aug. 26, 2011, now U.S. Pat. No. 8,436,163, which is a continuation of U.S. patent application Ser. No. 10/893,086, filed Jul. 16, 2004, which is a continuation of U.S. patent application Ser. No. 09/848,868, filed May 4, 2001, which claims the benefit of U.S. Provisional Patent Application Ser. No. 60/202,376, filed May 4, 2000, the entire disclosures of which are hereby incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 595710_SPT-8037CON6_SL.txt. The text file is 12,605 bytes, was created on Oct. 3, 2017, and is being submitted electronically via EFS-Web.

FIELD OF THE INVENTION

The present invention relates to therapeutic compositions and methods for inhibiting expression of full-length proteins in cells, and in particular to antisense compositions targeted against an mRNA sequence having its 5' end 1 to about 25 base pairs downstream of a normal splice acceptor junction in a preprocessed mRNA. Such targeting is effective to inhibit natural mRNA splice processing and produce splice variant mRNAs.

BACKGROUND OF THE INVENTION

Inhibition of protein expression by antisense targeting of DNA or RNA coding for the protein has been the subject of extensive study. Many reported procedures have employed phosphorothioate-linked oligonucleotides, which are charged, nuclease-resistant analogs of native DNA. The antisense mechanism involved is based on the activation of RNase, which cleaves the target nucleic acid to which the oligomer is bound. While these compounds have shown high activity, they also tend to show high levels of side effects, i.e. by cleavage of non-target RNA or by non-antisense mechanisms, such as nonspecific binding to proteins.

Another class of antisense oligomers, termed RNase-inactive, do not promote cleavage of bound RNA and are believed to act by sterically blocking the molecular machinery from transcribing, processing, or translating the target sequence. While these compounds tend to produce fewer side reactions, such as nonselective cleavage, than phosphorothioate oligomers, it has generally been necessary to target specific regions of RNA, such as the AUG start codon, for successful inhibition.

More recently, targeting of the splice acceptor junction of nuclear (unspliced) RNA by RNase-inactive oligomers has been reported. Kole and Dominski (U.S. Pat. No. 5,665,593) reported suppression of missplicing of β-globin RNA, in order to combat variants of β-thalassemia which result from such aberrant splicing. In this case, the aberrant splice junction was targeted, to direct splicing back to the normal site. R V Giles et al., *Antisense & Nucleic Acid Drug Dev.* 9:213-220 (1999), targeted a splice junction to induce missplicing of c-myc mRNA. In each of these cases, the region targeted is still somewhat restricted, in that the antisense oligomer spans the intron/exon splice junction of the pre-mRNA. Due to the advantages accorded by the use of uncharged, RNase-inactive oligonucleotides, a demonstration of further flexibility in targeting would be quite useful.

SUMMARY OF THE INVENTION

In one aspect, the invention provides an antisense compound, and a corresponding method of inhibiting normal splicing of preprocessed RNA in a eukaryotic cell, by contacting the cell with such an antisense compound. The compound is characterized by:

(a1): an uncharged morpholino backbone;
(a2): a base-sequence length of between 12 and 25 nucleotide bases; and
(a3): a base sequence that is complementary to a target region of a selected preprocessed mRNA coding for a selected protein, where the 5' end of the target region is 1-25 bases downstream of a normal splice acceptor site in the preprocessed mRNA, and having the properties that:

(b1): the compound is taken up by eukaryotic cells;
(b2): the compound hybridizes to the target region of preprocessed mRNA in such cells, and
(b3): the compound so hybridized to the target pre-mRNA prevents splicing at the normal acceptor splice site, such that the splice mechanism proceeds to a downstream splice acceptor site in the preprocessed mRNA, producing a splice variant processed mRNA with a truncated coding sequence.

In more specific embodiments, the 5' end of the target region is 2-20 bases, or 2-15 bases, downstream of the normal splice acceptor site. The length of the targeting compound is preferably about 15 to 20 nucleotide bases.

In one embodiment, the compound has intersubunit linkages selected from the group consisting of the structures presented in FIGS. 2-5. In preferred embodiments, the linkages are selected from a phosphorodiamidate linkage as represented at FIG. 3, where X=$NH_2$, NHR, or NRR', Y=O, and Z=O, and an alternate phosphorodiamidate linkage as represented at FIG. 3, where X=OR, Y=NH or NR, and Z=O. R and R' are groups which do not interfere with target binding. Preferably, R and R' are independently selected from alkyl and polyalkyleneoxy (e.g. PEG; $(CH_2CH_2O)_n$), or a combination thereof. The alkyl/polyalkyleneoxy chain may be substituted, preferably at the distal terminus, by a group selected from hydroxy, alkoxy, amino, alkylamino, thiol, alkanethiol, halogen, oxo, carboxylic acid, carboxylic ester, and inorganic ester (e.g. phosphate or sulfonate). Preferably, the chain (independent of substituents) is from 1 to 12 atoms long, and more preferably is from 1 to 6 atoms long. In selected embodiments, R and R' are independently methyl or ethyl. In one embodiment, X=$N(CH_3)_2$, Y=O, and Z=O.

NRR' may also represent a nitrogen heterocycle having 5-7 ring atoms selected from nitrogen, carbon, oxygen, and sulfur, and having at least as many carbon ring atoms as non-carbon ring atoms. Examples include morpholine, pyrrolidine, piperidine, pyridine, pyrimidine, pyrazine, triazine, triazole, pyrazole, pyrrole, isopyrrole, imidazole, oxazole, imidazole, isoxazole, and the like.

When the downstream splice acceptor site is a whole multiple of three bases downstream of the normal splice acceptor site, the splice variant mRNA has a coding sequence in frame with that of the processed mRNA when it is normally spliced.

The protein is preferably selected from the group consisting of myc, myb, rel, fos, jun, abl, bcl, p53, an integrin, a cathedrin, a telomerase, hCG, a receptor protein, a cytokine, a kinase, HIV rev, human papilloma virus, and human parvovirus B19. In selected embodiments, the protein is selected from myc, myb, abl, p53, hCG-β subunit, androgen receptor protein, and HIV-1 rev.

In further selected embodiments, the selected protein has multiple distinct binding regions, as in most transcription factors, and the truncated coding sequence codes for a variant protein in which one such binding region is disabled. Preferably, the variant protein is a dominant negative protein. One example is human c-myc, where the variant protein is an N-terminal truncated c-myc. In this embodiment, the antisense compound employed has a base sequence selected from the group consisting of SEQ ID NOs: 16 through 32 herein. The variant protein may also be a C-terminal altered c-myc, in which case the antisense compound employed can be an 18- to 20-mer having a base sequence which is a contiguous sequence selected from SEQ ID NO: 34; e.g. SEQ ID NO: 33.

In additional exemplary embodiments, the selected protein and the corresponding antisense base sequence(s) targeting its pre-mRNA are selected from the group consisting of:

(a) human chorionic gonadotropin, β subunit: a contiguous 18- to 20-nucleotide sequence selected from SEQ ID NO: 15; e.g. SEQ ID NO: 14;

(b) human androgen receptor: a contiguous 18- to 20-nucleotide sequence selected from SEQ ID NO: 9 or SEQ ID NO: 13; e.g. SEQ ID NO: 8 or 12, respectively;

(c) human p53: a contiguous 18- to 20-nucleotide sequence selected from SEQ ID NO: 36; e.g. SEQ ID NO: 35;

(d) human abl: a contiguous 18- to 20-nucleotide sequence selected from SEQ ID NO: 38; e.g. SEQ ID NO: 37; and (e) HIV-1 rev: a contiguous 18- to 20-nucleotide sequence selected from SEQ ID NO: 41; e.g. SEQ ID NO: 40.

These and other objects and features of the present invention will become more fully apparent when the following detailed description of the invention is read in conjunction with the accompanying drawings.

DETAILED DESCRIPTION OF THE INVENTION

I. Definitions

The terms below, as used herein, have the following meanings, unless indicated otherwise:

"Antisense" refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence, typically with an mRNA. The oligomer may have exact sequence complementarity to the target sequence or near complementarity. These antisense oligomers may block or inhibit translation of the mRNA, and/or modify the processing of an mRNA to produce a splice variant of the mRNA.

As used herein, the terms "compound", "agent", "oligomer" and "oligonucleotide" may be used interchangeably with respect to the antisense oligonucleotides of the invention.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. Exemplary structures for antisense oligonucleotides for use in the invention include the morpholino subunit types shown in FIGS. 1A-1E, with the linkages shown in FIGS. 2-5. Such structures are described, for example, in Hudziak et al., *Antisense Nucleic Acid Drug Dev.* 6, 267-272 (1996) and Summerton and Weller, *Antisense Nucleic Acid Drug Dev.* 7, 187-195 (1997).

Figure 1A:
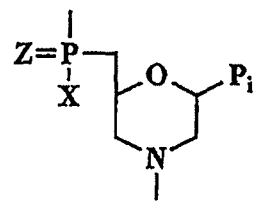
FIGS. 1A-1E show several preferred subunits having 5-atom (A), six-atom (B) and seven-atom (C-E) linking groups suitable for forming polymers.
Figure 1B:
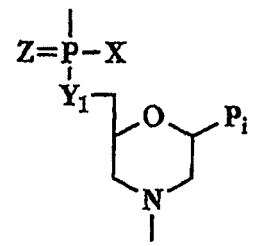
Figure 2:
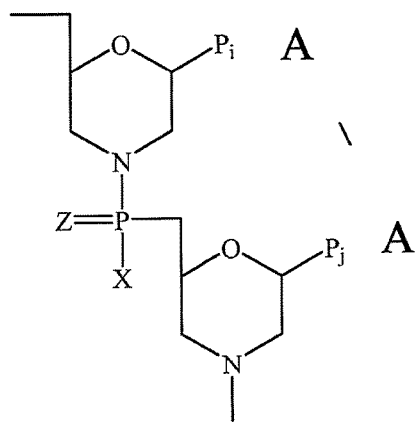
FIG. 2 shows the repeating subunit segment of exemplary morpholino oligonucleotides, designated A-A, constructed using subunit A of FIG. 1A.

Subunit A in FIG. 1A contains a 1-atom phosphorous-containing linkage which forms the five atom repeating-unit backbone shown at A-A in FIG. 2, where the morpholino rings are linked by a 1-atom phosphoamide linkage.

Figure 3:
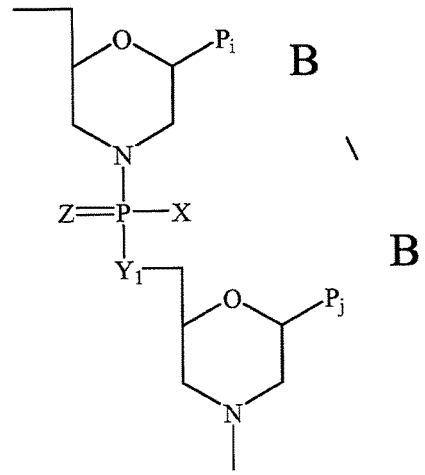
FIG. 3 shows the repeating subunit segment of exemplary morpholino oligonucleotides, designated B-B, constructed using subunits B of FIG. 1B.

A preferred morpholino oligonucleotide is composed of morpholino subunit structures of the form shown in FIG. 3, where the structures are linked together by phosphorodiamidate linkages, joining the morpholino nitrogen of one subunit to the 5' exocyclic carbon of an adjacent subunit, and Pi and Pj are purine or pyrimidine base-pairing moieties effective to bind, by base-specific hydrogen bonding, to a base in a polynucleotide. In preferred embodiments, the linkages are selected from a phosphorodiamidate linkage as represented at FIG. 3, where $X=NH_2$, NHR, or NRR', $Y=O$, and $Z=O$, and an alternate phosphorodiamidate linkage as represented at FIG. 3, where $X=OR$, $Y=NH$ or NR, and $Z=O$. R and R' are groups which do not interfere with target binding. Preferably, R and R' are independently selected from alkyl and polyalkyleneoxy (e.g. PEG; $(CH_2CH_2O)_n$), or a combination thereof. (An example of such a combination would be $-(CH_2)_3(CH_2CH_2O)_3-$). The alkyl/polyalkyleneoxy chain may be substituted, preferably at the distal terminus (i.e. the terminus not connected to the oligomer backbone), by a group selected from hydroxy, alkoxy, amino, alkylamino, thiol, alkanethiol, halogen, oxo, carboxylic acid, carboxylic ester, and inorganic ester (e.g. phosphate or sulfonate). Preferably, the chain (independent of substituents) is from 1 to 12 atoms long, and more preferably is from 1 to 6 atoms long. In selected embodiments, R and R' are independently methyl or ethyl. In one embodiment, X=N (CH$_3$)$_2$, Y=O, and Z=O. NRR' may also represent a nitrogen heterocycle having 5-7 ring atoms selected from nitrogen, carbon, oxygen, and sulfur, and having at least as many carbon ring atoms as non-carbon ring atoms. Examples include morpholine, pyrrolidine, piperidine, and pyridine.

Figure 1C:
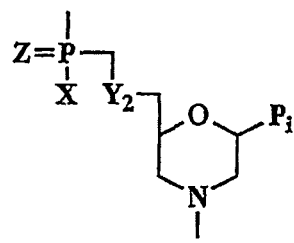
Figure 1D:
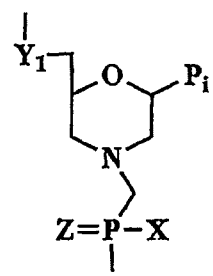
Figure 1E:
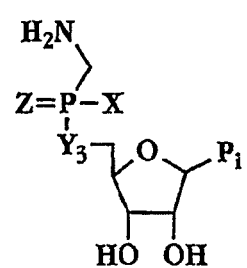
Figure 4:
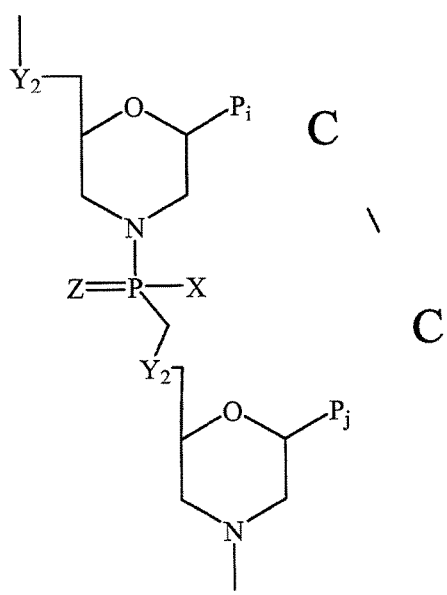
FIG. 4 shows the repeating subunit segment of exemplary morpholino oligonucleotides, designated C-C, constructed using subunits C of FIG. 1C.
Figure 5:
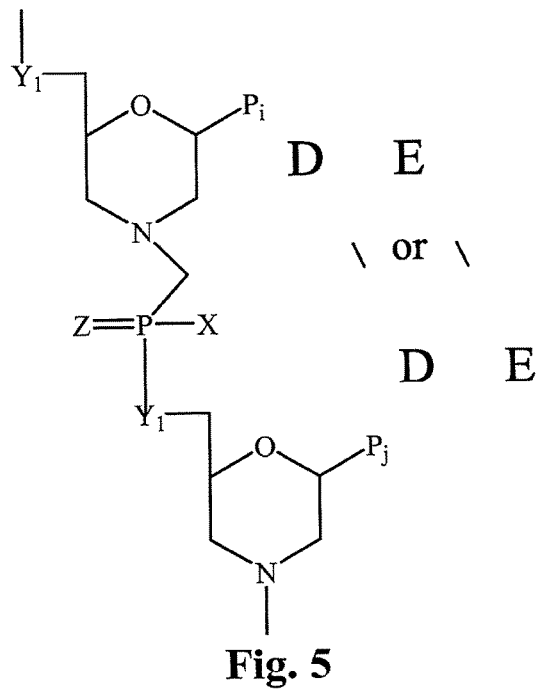
FIG. 5 shows the repeating subunit segment of exemplary morpholino oligonucleotides, designated D-D or E-E, constructed using subunits D or E of FIG. 1D or FIG. 1E, respectively.

Subunits C-E in FIGS. 1C-1E are designed for 7-atom unit-length backbones as shown for C-C in FIG. 4, and D-D and E-E in FIG. 5. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR. In all subunits depicted in FIGS. 1A-1E, Z is O or S, and P$_i$ or P$_j$ is adenine, cytosine, guanine or uracil.

A "nuclease-resistant" oligomeric molecule (oligomer) is one whose backbone is not susceptible to nuclease cleavage.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.-80° C. or higher. Such hybridization preferably corresponds to stringent hybridization conditions, selected to be about 10° C., and preferably about 50° C. lower than the thermal melting point (T[m]) for the specific sequence at a defined ionic strength and pH. At a given ionic strength and pH, the T[m] is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

A "RNase-inactive" or "RNase-incompetent" oligonucleotide or oligonucleotide analog is one which acts via an RNase-independent mechanism, unlike RNase-active oligonucleotides, such as phosphorothioates. They are believed to function by sterically blocking target RNA formation, nucleocytoplasmic transport or translation, and are thus also referred to as "steric blockers". This class includes, for example, methylphosphonates, morpholino oligonucleotides, as described herein, peptide nucleic acids (PNA's), and 2'-O-allyl or 2'-O-alkyl modified oligonucleotides.

In a "peptide nucleic acid", the deoxyribose phosphate units of an oligonucleotide backbone are replaced with polyamide linkages. Proper backbone spacing is attained by the use of 2-aminoethyl glycine units, with a nucleotide base attached to each 2-amino group via a methylenecarbonyl group.

A "2'-O-allyl (or alkyl) modified oligonucleotide" is an oligoribonucleotide in which the 2' hydroxyl is converted to an allyl or alkyl ether. The alkyl ether is typically a methyl ether.

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Lower alkyl" refers to an alkyl radical of one to six carbon atoms, and preferably one to four carbon atoms, as exemplified by methyl, ethyl, isopropyl, n-butyl, isobutyl, and t-butyl.

A "truncated" protein or coding sequence has some portion of the normal protein or sequence removed from one or the other terminus, from an internal region, or a combination of the above.

An amino-truncated (N-truncated) or carboxy-truncated (C-truncated) protein is one having an abnormal or deleted amine terminus or carboxy terminus, respectively, arising from translation of a splice variant mRNA.

II. Antisense Compounds

In accordance with the present invention, it has been discovered that an antisense compound having from 12 to 25 nucleotides, including a targeting base sequence that is complementary to a target region of a selected preprocessed mRNA coding for a selected protein, where the 5' end of the target region is 1 to 25 bases downstream, preferably 2 to 20 bases downstream, and more preferably 2 to 15 bases downstream, of a normal splice acceptor site in the preprocessed mRNA, is effective to inhibit splicing at the normal splice acceptor site and thus produce splice variant mRNA, leading to truncated or otherwise aberrant versions of the selected protein upon translation. Advantages of this strategy are set forth below.

The antisense compound employed in the present invention is one that does not activate RNase H. RNase-H active oligomers, of which phosphorothioate oligonucleotides are the most prominent example, operate primarily by a mechanism in which the target mRNA is cleaved. RNase-incompetent oligomers, on the other hand, are believed to act by a steric blocking mechanism. Such compounds include morpholino oligomers, PNA's (peptide nucleic acids), methylphosphonates, and 2'-O-alkyl or -allyl modified oligonucleotides, all of which are known in the art. The preferred antisense oligomers (compounds) of the present invention are morpholino oligomers, which are composed of morpholino subunits of the form shown in U.S. Pat. Nos. 5,698,685, 5,217,866, 5,142,047, 5,034,506, 5,166,315, 5,521,063, and 5,506,337, all of which are incorporated herein by reference. The synthesis, structures, and binding characteristics of morpholino oligomers are detailed in these patents. In a morpholino oligomer, (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. As shown in the reference, several types of nonionic linkages may be used to construct a morpholino backbone.

Such morpholino oligomers have shown high binding affinity for RNA targets, and the uncharged backbone favors uptake into cells and reduces non-specific binding interactions, relative to charged analogs such as phosphorothioates. They have been shown to provide significantly improved activity and selectivity in inhibiting translation of targeted sequences in comparison to phosphorothioate oligonucleotides. See, for example, Summerton et al., *Antisense & Nucleic Acid Drug Dev.* 7(2):63-70, April 1997. The morpholino oligomers have very high nuclease resistance and good water solubility, making them good candidates for in vivo use. Efficient uptake by cells in vivo is demonstrated in co-owned and copending application Ser. No. 09/493,427 and the corresponding PCT Pubn. No. WO 0044897. As described therein, morpholino oligonucleotides having phosphoramidate linkages formed heteroduplexes with target RNA, which are protected in this duplex state from nuclease degradation. Such a duplex is expelled from the cell, and the target RNA can later be detected in a body fluid sample from the subject. These results demonstrated that the morpholino oligomers (i) migrate to and enter cells in the body and (ii) bind with high affinity, via Watson-Crick base-pairing, to target nucleic acid regions.

Exemplary backbone structures for antisense oligonucleotides of the invention include the β-morpholino subunit types shown in FIGS. 1A-1E, as described above. It will be appreciated that a polynucleotide may contain more than one linkage type.

A preferred morpholino oligonucleotide is composed of morpholino subunit structures of the form shown in FIG. 3, where the structures are linked together by phosphorodiamidate linkages, joining the morpholino nitrogen of one subunit to the 5' exocyclic carbon of an adjacent subunit, $P_i$ and $P_j$ are purine or pyrimidine base-pairing moieties effective to bind, by base-specific hydrogen bonding, to a base in a polynucleotide. In preferred embodiments, the linkages are selected from a phosphorodiamidate linkage as represented at FIG. 3, where X=$NH_2$, NHR, or NRR', Y=O, and Z=O, and an alternate phosphorodiamidate linkage as represented at FIG. 3, where X=OR, Y=NH or NR, and Z=O. R and R' are groups which do not interfere with target binding. Preferably, R and R' are independently selected from alkyl and polyalkyleneoxy (e.g. PEG; $(CH_2CH_2O)_n$), or a combination thereof. The alkyl/polyalkyleneoxy chain may be substituted, preferably at the distal terminus, by a group selected from hydroxy, alkoxy, amino, alkylamino, thiol, alkanethiol, halogen, oxo, carboxylic acid, carboxylic ester, and inorganic ester (e.g. phosphate or sulfonate). Preferably, the chain (independent of substituents) is from 1 to 12 atoms long, and more preferably is from 1 to 6 atoms long. In selected embodiments, R and R' are independently methyl or ethyl. In one embodiment, X=$N(CH_3)_2$, Y=O, and Z=O. NRR' may also represent a nitrogen heterocycle having 5-7 ring atoms selected from nitrogen, carbon, oxygen, and sulfur, and having at least as many carbon ring atoms as non-carbon ring atoms. Examples include morpholine, pyrrolidine, piperidine, pyridine, pyrimidine, pyrazine, triazine, triazole, pyrazole, pyrrole, isopyrrole, imidazole, oxazole, isoxazole, and the like.

The solubility of the antisense compound, and the ability of the compound to resist precipitation on storage in solution, can be further enhanced by derivatizing the oligomer with a solubilizing moiety, such as a hydrophilic oligomer, or a charged moiety, such as a charged amino acid or organic acid. The moiety may be any biocompatible hydrophilic or charged moiety that can be coupled to the antisense compound and that does not interfere with compound binding to the target sequence. The moiety can be chemically attached to the antisense compound, e.g., at its 5' end, by well-known derivatization methods. One preferred moiety is a defined length oligo ethylene glycol moiety, such as triethyleneglycol, coupled covalently to the 5' end of the antisense compound through a carbonate linkage, via a piperazine linking group forming a carbamate linkage with triethyleneglycol, where the second piperazine nitrogen is coupled to the 5'-end phosphorodiamidate linkage of the antisense. Alternatively, or in addition, the compound may be designed to include one a small number of charged backbone linkages, such as a phosphodiester linkage, preferably near one of the ends of the compound. The added moiety is preferably effective to enhance solubility of the compound to at least about 30 mgs/ml, preferably at least 50 mgs/ml in aqueous medium.

The compound is designed to hybridize to the target sequence under physiological conditions with a $T_m$ substantially greater than 37° C., e.g., at least 50° C. and preferably 60° C.-80° C. Although the compound is not necessarily 100% complementary to the target sequence, it is effective to stably and specifically bind to the target sequence such that expression of the target sequence, is modulated. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained.

III. Selection of Target Sequences

A. RNA Splicing: Background

The processing of nuclear RNA following transcription is observed in virtually all living cells. The mammalian genome contains genes that make transcripts of approximately 16,000 bases in length containing 7 to 8 exons. The process of splicing reduces the length of the mRNA to an average of 2,200 bases. The initial transcript is referred to as heterologous nuclear RNA (hnRNA) or pre-mRNA. Processing of hnRNA involves an aggregate of approximately 20 proteins, referred to collectively as the spliceosome, which carries out splicing and transport of mRNA from the nucleus. The spliceosome does not appear to scan from a common direction for all transcripts; introns may be removed in a reproducible order but not in a directional order. For example, introns 3 and 4 may be removed first, followed by removal of introns 2 and 5, followed by removal of introns 1 and 6. The order of intron removal is not predictable a priori of observation. The sequence recognition for processing is small, suggesting that errors or multiplicity of processing sites can be anticipated, and, in fact, as more genes are investigated, more variation in processing of hnRNA has been observed.

In preprocessed mRNA, the two-base sequence motifs at exon/intron junctions are invariant. The upstream (5') splice donor (SD) junction is of the form exon-/GT-intron, while the downstream (3') splice acceptor (SA) junction is of the form intron-AG/exon. The flanking bases are not invariant; however, the base immediately upstream of the splice acceptor AG sequence is C about 80% of the time.

The current understanding of intron sequence recognition is as follows:

```
5'-exonA(64)G(73)/G(100)T(100)A(62)A(68)G(84)T(63) . . . TACTAAC . . . C(80)A(100)G(100)/exon-NN . . . -3'
         splice donor (SD)                                                    splice acceptor (SA)
```

The numbers in parenthesis represent the approximate (when <100%) percent utilization of a base at a site. The bold A in the middle of the intron is the site (branch point) at which the G from the splice donor forms a branched 2'-5'-structure referred to as the lariat. The sequence indicated (TACTAAC) is the consensus observed in yeast. The consensus sequence in mammalian cells is $PyNPy_{(80)}Py_{(87)}Pu_{(75)}APy_{(75)}$, where Py represents a pyrimidine (U/T or C) and Pu represents a purine (A or G). The A at the branch point is invariant, and is typically found about 12 to 50 bases upstream of the AG site. A pyrimidine-rich region (not shown above) is also generally found near the 3' end of the intron, about 10-15 bases upstream of the AG site.

Once the spliceosome forms the lariat, two transesterification reactions take place: 1) the 2'-OH of the branch point A in the intron to the 5'-phosphate of the SD intron G, and 2) the 3'-OH of the SD exon G to the 5'-phosphate of the first base of the SA exon. The removed intron is rapidly degraded in most cases, and the joined exons are now referred to as mature mRNA, which is transported out of the nucleus for translation into proteins by the ribosome.

B. Targeting Strategies

Various approaches could be taken to targeting the processing (splicing) of mRNA by antisense oligomers. The following sites could be targeted:

1. The exon-only portion of the SD exon (upstream of SD site), to interfere with SD processing.

2. The SD exon/intron junction, to interfere with SD processing.

3. The site of lariat formation within the intron, to block spliceosomal recognition upstream of the SA exon.

4. The SA intron/exon junction, to interfere with SA processing.

5. The exon-only portion of the SA exon (downstream of SA site), to interfere with SA processing.

Prior art methods have utilized strategy 2 or 4 (targeting of SD or SA junction). See, for example, RV Giles et al., cited above, in which a morpholino antisense oligomer spanning a splice acceptor site in the c-myc gene is described.

Experiments in support of the present invention found that targeting strategies 4 and 5 above, directed to the splice acceptor, were more reliably effective than strategies 1 and 2, directed to the splice donor.

For example, studies were carried out with rat CYP3A2 pre-mRNA targeted in vivo (whole animal). Animals were injected i.p. with 100 μg PMO (as shown in FIG. 3, where $Y_1$ and Z are oxygen and X is $N(CH_3)_2$) in phosphate buffered saline. The diminished rate of microsomal metabolism of erythromycin O-demethylase was monitored to reflect the expected phenotype caused by the antisense inhibition. As shown, the splice donor (SD) targeting was less effective than the splice acceptor (SA) strategy.

| STRATEGY | ANTISENSE SEQUENCE (/ indicates splice junction) | SEQ ID NO: | ERDEM % of control |
|---|---|---|---|
| Control | Saline | — | 100 ± 10.2 (N = 7) |
| SD | 3'-AAGAGATGGC/CACTCACTGG-5' | 4 | 94.7 ± 5.4 (N = 3) |
| SA | 3'-GGAAATATC/TGAACCTTGGG-5' | 5 | 86.5 ± 3.8 (N = 3) |

Experiments with oligomers antisense to c-myc mRNA were conducted in cultured rat NRK cells, evaluating the inhibition of cellular DNA synthesis by monitoring incorporation of tritiated thymidine. Sequences were derived from Genbank Acc. No. Y00396 (rat) and J00120 (human), targeting the splice acceptor region at the beginning of exon 2 (with the exception of SEQ ID NO: 1, which targets the splice donor). The rat and human sequences indicated are highly homologous in this region. The oligomers listed in Table 1, below, were screened for antiproliferative effects using several proliferation assays. Primary fibroblasts from two species, rat and human, NRK and WI-38, respectively, were used for the screening. Data shown in Table 1 employed NRK cells.

Data from [$^3$H]thymidine incorporation assays using 20 μM PMO (as shown in FIG. 3, where $Y_1$ and Z are oxygen and X is $N(CH_3)_2$) are presented in Table 1. Percentages refer to [$^3$H]thymidine incorporation relative to the vehicle ($H_2O$) control. Therefore, the lower the number, the greater the antiproliferative effect. It can be seen that all oligomers tested exhibited at least some antiproliferative activity. The extent of the inhibitory activity compared favorably with the antiproliferative drug Taxol (Paclitaxel, Bristol-Myers Squibb, Princeton, N.J.) at 32% of control. As 10%-20% of the cells are not affected by the scrape loading procedure and will, therefore, contribute to the residual [$^3$H]thymidine incorporation activity, it is likely that most or all cells containing the most efficacious oligomers were growth inhibited.

SEQ ID NO: 45, which spans the 3'-splice acceptor site of the first intron of human myc pre-mRNA, was shown by Giles et al. (1999) to cause missplicing of myc pre-mRNA. A cryptic or latent splice acceptor, 44 bp distal to the normal splice acceptor position, was used to produce an aberrantly spliced mRNA with a 44-bp deletion. This misspliced mRNA lacks the initiator AUG and did not produce a normal myc protein.

SEQ ID NO: 25 does not span the intron 1-exon 2 boundary, the first potential complementary base pair being the tenth nucleotide from the 3' splice acceptor. Similarly, SEQ ID NO: 3 has its 5' end eleven bases downstream of the splice acceptor in the rat c-myc mRNA sequence. As the data shows, both sequences were effective in inhibiting cell growth.

It was of interest to determine if these oligomers inhibited normal splicing, as had been shown for SEQ ID NO: 45. Accordingly, RNA was prepared from human cells treated with positive (SEQ ID NO: 45) and negative (SEQ ID NO: 50) control oligomers as well as SEQ ID NO: 25. The structure of the RNA was then analyzed by making a DNA copy with reverse transcriptase and then performing PCR with flanking DNA primers (see Materials and Methods, below). The products of the RT-PCR procedure were analyzed by agarose gel electrophoresis.

In untreated or irrelevant oligomer-treated cells, a 304-bp band is predicted, and was observed, from the primers used and the c-myc nucleotide sequence. For cells treated with SEQ ID NO: 25, two DNA bands were observed. The upper band, which comigrated with the fragment from untreated or negative control cells, represented mRNA from the 10%-20% of cells not scrape loaded by the uptake procedure used, plus the fraction of correctly spliced mRNA in treated cells. The heavier lower band represented the misspliced, 44-bp depleted mRNA.

TABLE 1

Cell Growth Inhibition by Anti-c-myc and Control Sequences

| SEQ ID NO: | Antisense Sequence (5' → 3') | Targeted Region* | Incorporation vs. vehicle control |
|---|---|---|---|
| 1 | CTGTGCTTAC/CGGGTTTTCCACCTCCC (/ = SD site) | 2553-2579 | 51 ± 8% |
| 2 | ATCGTCGTGACTG/CTGTTGGAGGG (/ = SA site) | 4140-4164 | 27 ± 3% |
| 3 | GCTCACGTTGAGGGGCATCG | 4161-4180 | 38 ± 2% |
| 25 | ACGTTGAGGGGCATCGTCGC | J00120 4515-34 | 29% |
| 42 | GGGGCAUCGUCGUGACUGU/CUGUUGGAGGG | 4140-4169 | 20% |
| 43 | CGUCGUGACUGU/CUGUUGGAGG | 4141-4162 | 45% |
| 44 | CGTCGTGACTGT/CTGTTGGAGG | 4141-4162 | 21% |
| 45 | GGCAUCGUCGCGGGAGGCUG/CUGGAGCG | J00120 4498-4505 | 22% |
| 46 | CCGCGACAUAGGACGGAGAGCAGAGCCC | 4364-4391 | 56% |
| 47 | ACTGTGAGGGCGATCGCTGC (scrambled) | — | ~100% |
| 48 | ACGATGAGTGGCATAGTCGC (3 mismatches) | — | >100% |
| 49 | CTCCGCAATGCTGAAAGGTG (rat BCL-2) | — | >100% |
| 50 | GGCGUGCCUCAAACAUGGUGGCGG (rat PCNA-1) | — | ~100% |

*Genbank Y00396 (rat) unless otherwise indicated

Two irrelevant-sequence oligomers (rat BCL-2, SEQ ID NO: 49 and rat PCNA-1, SEQ ID NO: 50) did not inhibit NRK cells at the highest concentration assayed (20 μM). Mismatched and scrambled sequences of SEQ ID NO: 25 (SEQ ID NOs 48 and 47, respectively) had no effect on the proliferation of WI-38 (human) fibroblasts at 20 μM.

Cells loaded with SEQ ID NO: 25 also produced two bands from the RT-PCR procedure, one the size of normally spliced mRNA and one smaller. It can therefore be concluded that SEQ ID NO: 25, despite not directly overlapping the splice acceptor site, is capable of causing missplicing. The irrelevant PMO (SEQ ID NO: 50) gave an mRNA structure pattern identical to that of untreated cells, demonstrating that the missplicing is sequence specific.

A dose-response study with SEQ ID NO: 25 gave an $IC_{50}$ of 3 µM. The inhibitory effects began to plateau at 10 µM, and there was little further change from 10 µM to 20 µM.

Myc protein has been implicated as important for the transition from $G_0/G_1$ of the cell cycle into the S phase (MK Mateyak et al., *Cell Growth Differ.* 8:1039-48, 1997). It could, therefore, be expected that if myc protein levels are reduced, the cells would arrest in $G_1$. This effect was investigated by determining the number of cells in $G_1$ and $G_2$, using the method of Telford et al. (*Cytometry* 13:137-43, 1993) (see Materials and Methods). After removal of RNA by hydrolysis, cells were stained by propidium iodide, a DNA-specific fluorescent dye. The DNA content per cell distribution was then determined by FACS analysis. The FACS intensity profiles show two peaks, corresponding to 2N DNA content ($G_1$) and 4N DNA ($G_2$). Cells treated with the PMO having SEQ ID NO: 25 showed an increase in the proportion of cells in G1 (79% compared to 66% vehicle control) compared with those in $G_2$ (9% compared to 21% vehicle control). A positive control of quiescent cells obtained by growth factor starvation showed 80% of cells in $G_1$ and 8% in $G_2$.

To obtain further evidence that the anti-c-myc oligomer SEQ ID NO: 25 inhibits c-myc mRNA expression by an antisense mechanism, a reporter gene model system was constructed to directly examine one gene (luciferase) and its activity (light production). The myc-luciferase reporter plasmid contained the entire 2.2-kb 5' region of human c-myc and the first 6 amino acid codons of the myc protein fused to the insect luciferase cDNA (see Hudziak et al., *Antisense Nucleic Acid Drug Dev.* 10:163-76 (2000). It was transfected into HeLa cells, and a luciferase-producing clone was selected and designated clone L6. This cell line was scrape loaded with the indicated concentrations of PMO and replated. After 24-30 hours, the cells were lysed, and luciferase activity was measured (see Materials and Methods).

The results showed strong inhibition of luciferase production, with an $IC_{50}$ of 300 nM. Several control experiments were performed to determine if the observed inhibition of luciferase synthesis was due to sequence-specific inhibition by the PMO. SEQ ID NO: 25 and the two sequence permutations noted above (SEQ ID NOs: 47 and 48) were compared. Neither the scrambled version nor the 3-base mispair oligomer had any effect on luciferase production. Other control experiments showed that SEQ ID NO: 25 had no effect on HeLa proliferation during the 30-hour incubation time of the luciferase assay, and had no effect on an unrelated target reporter system (rabbit a-globin; J Summerton et al., *Antisense & Nucleic Acid Drug Dev.* 7:63-70, 1997) under conditions where a sequence complementary agent gave 70% inhibition. Other sequences containing 3-4 contiguous guanine (G) bases were tested in the NRK cell proliferation assay described above, and gave no significant inhibition of cell proliferation at concentrations up to 20 µM.

In an evaluation of the "functional footprint" of PMO antisense directed to the splice acceptor (SA) region of rat c-myc, interference in splicing was observed with PMOs targeting the region from −44 upstream of the SA to +36 downstream (3' end of target region) from the SA. As the target sequence moved downstream, the proportion of lower molecular weight proteins, relative to normal c-myc, was observed to increase.

Targeting downstream of the splice acceptor junction, i.e. within the exon, is generally preferred, for reasons discussed below.

IV. Consequences of Interference with SA Site

If a binding oligomer interferes with normal mRNA splicing at the SA site, the spliceosome will proceed to the next best unblocked candidate site in the region. This site tends to be a [C]AG sequence with a short run of pyrimidines 10 to 15 bases upstream and a suitable branch point further upstream.

The resulting processed mRNA will generally be a splice variant mRNA in which the sequence between the normal splice acceptor site and the alternate (or "cryptic") splice acceptor site has been deleted. The resulting variant protein can take different forms depending on the deleted sequence. For example, if the deleted sequence contains a whole multiple of three base pairs (that is, the downstream splice acceptor site is a whole multiple of three bases downstream of the normal splice acceptor site), the subsequent sequence will be in frame with the normal sequence, and a truncated form of the native protein will result. This permits the formation of dominant negative proteins, as described, for example, in Example C below. If the cryptic site is out of frame with the normal site, however, an unrelated "nonsense" protein will be produced. Due to the frequent occurrence of stop codons in non-reading frame sequences (about one per twenty codons), such a splice variant mRNA typically results in early termination of translation.

If the deleted sequence includes an AUG start site, translation may then occur at an alternate AUG site found further downstream. Again, if this alternate site is in frame with the normal AUG site, the resulting protein will have a deletion of some number of amino acids from the native protein. If the alternate site is out of frame, a "nonsense" protein, typically truncated early in translation, will result.

In one embodiment, exemplified in Examples A and B below, a carboxy-terminal truncated protein is created. In another embodiment, exemplified in Examples C and D below, a protein having an abnormal or deleted amino terminus is produced. The latter can be accomplished if the AUG translation start site is in exon 2 or greater of the mRNA.

Thus, when the sequence of pre-mRNA for a desired protein is known, an antisense target can be designed to alter desired regions of the protein. Preferably, the binding domains of the protein are also known, such that selected functions of the protein can be altered.

The following steps can be used to target genes with multiple exons, in accordance with the invention:

Step 1. Identify functional domains of the protein in question. The scientific literature can provide most of this information. One excellent source is "The Oncogene Factsbook" by Robin Hesketh, Academic Press, London, 1995, in which proteins related to cancer are reviewed and their functional domains mapped. Similarly, the "Cytokine Factsbook" (RE Callard and AJH Gearing, Academic Press) describes functional domains of cytokines. Other works in the same series include "The Protein Kinase Factsbook", "The G-Protein Linked Receptor Factsbook", and "The Extracellular Matrix Factsbook".

Step 2. Search GenBank or similar nucleic acid databases for the gene sequence, including exon/intron sequences and junctions.

Step 3. Preferred antisense targets are within approximately 35-40 downstream bases of a splice acceptor site. Preferably, the target region has its 5' end at a location 1 to 25 bases downstream, more preferably 2 to 20 bases downstream, and most preferably 2 to 15 bases downstream, from the SA junction. (Note that a sequence one base downstream directly abuts, but does not overlap, the [C]AG splice acceptor site, and includes the first base of the normal exon.)

Step 4. To predict the consequence of inhibition, search the exon downstream of the SA for a cryptic splice acceptor, i.e. a [C]AG sequence downstream from the authentic SA. Once such a candidate site is located, search for a 5'-TACTA AC-3' (or similar) site for lariat formation 12 to 50 bases upstream of the cryptic SA. (Note that, according to the consensus sequence given above, only the branch point A must be conserved, so there is considerable flexibility in this sequence.) Preferably, there should also be a short pyrimidine-rich region 10-15 bases upstream of the cryptic SA.

Step 5. Once a potential cryptic SA site is identified, determine if its use will result in "in frame reading" by dividing the number of bases between the authentic site and the cryptic site by 3. If the quotient is a whole number, then the resultant protein will be "in frame" and possibly a dominant negative protein (see below).

Accordingly, in one preferred embodiment, an antisense target is chosen such that splicing is likely to be directed to a cryptic site whose use will result in in-frame reading.

V. Target Proteins and Selected Examples

Suitable target proteins include, for example, transcription factors, particularly oncogenic or proto-oncogenic proteins such as myc, myb, rel, fos, jun, abl, bcl, and p53; matrix proteins, such as integrins and cathedrins; other tumor-expressed proteins, such as hCG; telomerases; receptor proteins; cytokines; kinases; and viral proteins, such as HIV rev, human papilloma virus, and human parvovirus B19. It is appreciated that inhibition of such proteins has numerous therapeutic applications. These include, but are not limited to, antitumor therapy, e.g. by targeting proteins, such as transcription factors, involved in various aspects of cell division and cell cycle regulation; antiviral or antibacterial therapy, by targeting proteins essential to replication or other vital functions of the infectious agent; and inhibition of restenosis or other proliferative disorders, by inhibiting proteins which support cell proliferation at the site.

Transcription factors are typically multidomain proteins, having a DNA binding region and a protein-protein binding region. Interfering with one of these regions can produce a dominant negative protein, which counters the activity of the native protein by preserving one activity (such as protein binding) while inhibiting another activity critical to the proper function of the protein (such as DNA binding; or vice versa). See the c-myc example described below.

As noted above, functional domains of many of the target proteins noted above have been studied extensively and reported in the literature. Sequences of pre-mRNA, including locations of introns, exons, and AUG start codons, can be found in the GenBank sequence database or other published sources readily available to those of skill in the art.

Following are several examples of antisense targeting downstream of splice acceptor domains in selected proteins to produce splice variants mRNAs which, upon translation, produce proteins with specific alterations.

In one embodiment, exemplified in Examples A and B, a carboxy-terminal truncated protein is created. In another embodiment, exemplified in Examples C and D, a protein having an abnormal or deleted amino terminus is produced.

A. Human Androgen Receptor (GenBank M35845, M35846)

A review of prostate cancer molecular biology indicates that androgen ablation is the state of the art therapy. In accordance with the present invention, this can be accomplished by inactivation of the androgen receptor. By targeting the center of the gene, at exon 2, various options are available for inhibiting expression of a functional androgen receptor. Proposed targeting of the splice acceptor in exon 2 (SEQ ID NO: 8; GenBank M35845) or exon 3 (SEQ ID NO: 11; GenBank M35846) is indicated.

```
End of     5'-. . . TGTGTCTTTTCCAG/ ← splice acceptor site (SEQ ID NO: 6)
Intron 1:

Exon 2:    5'-TTTGGAGACTGCCAGGGACCATG . . .-3'            (SEQ ID NO: 7)

Target     5'-CATGGTCCCTGGCAGTCTCC-3'                     (SEQ ID NO: 8)
antisense
sequence:
```

This oligomer (SEQ ID NO: 8) targets the sequence starting at base 48, four bases downstream of the normal splice acceptor site. The next probable cryptic splice site is at base 100 (CAG at 97-99; branch point A at 80; upstream pyrimidine region at 87-92. This site is out of frame with the normal site and should thus result in early termination of the protein.

Similar length oligomers targeting sequences having a 5' end 1 to about 18 bases downstream of the splice acceptor could also be used. This includes oligomers having a length of about 18 contiguous nucleotides selected from the sequence 5'-TCA ATG GGC AAA ACA TGG TCC CTG GCA GTC TCC AAA-3' (SEQ ID NO: 9; complementary to bases 45-80 of the sequence given in Genbank Acc. No. M35845).

```
End of       5'-. . . TTTGTGTTCTCCCAG/← splice acceptor site (SEQ ID NO: 10)
intron 2:

Exon 3:      5'-GGAAACAGAAGTACCTGTGCGCC . . .-3'            (SEQ ID NO: 11)
Antisense    5'-GGC GCA CAG GTA CTT CTG-3'                  (SEQ ID NO: 12)
```

This oligomer (SEQ ID NO: 12) targets the sequence starting at base 49, six bases downstream of the normal splice acceptor site. A possible cryptic splice site is at base 145 (CAG at 143-145; branch point A at 114; pyrimidine region at 123-127). This site is in frame with the normal splice site and should thus result in a carboxy-truncated version of the native protein.

Similar length oligomers targeting sequences having a 5' end 1 to about 18 bases downstream of the splice acceptor could also be used. This includes, for example, oligomers having a length of about 18-20 contiguous nucleotides selected from the sequence 5'-AAT CAT TTC TGC TGG CGC ACA GGT ACT TCT GTT TCC-3' (SEQ ID NO: 13; complementary to bases 44-79 of the sequence given in GenBank Acc. No. M35846).

B. Human chorionic gonadotropin (β subunit) (GenBank X00266)

The β subunit of hCG is nearly identical to leutinizing hormone (LH) with the exception of the COOH end, which is extended in hCG. This extension is in exon 3 of the gene. By interfering with the exon 3 SA site, hCG could be truncated without targeting LH, unlike targeting of the AUG translation initiation sites, which are highly conserved in both proteins.

An oligomer with the sequence 5'-CCC CTG CAG CAC GCG GGT-3' (SEQ ID NO: 14) binds in exon 3 near (directly abutting) the SA (CAG at 1318-1320), targeting the sequence from bases 1321-1338, and interferes with splicing at this site Similar length oligomers targeting sequences having a 5' end at base 1322, 1323, etc., up to about base 1340, could also be used. This includes, for example, oligomers having a length of about 18-20 contiguous nucleotides selected from the sequence 5'-GAG GCA GGG CCG GCA GGA CCC CCT GCA GCA CGC GGG T-3' (SEQ ID NO: 15; complementary to bases 1321-57 of the sequence given in Genbank Acc. No. X00266).

Possible cryptic SA sites are at base 1393 (AG at 1391-2; branch point A at 1370 or 1373; in frame) and at 1458 (CAG at 1455-7; branch point A at 1427; out of frame). Splicing at either site would delete at least 24 amino acids from the protein, and possibly more, if the out of frame site were used. Since hCG is expressed only in tumor cells, this would be therapeutically beneficial in that less protein is expressed, and the protein will have a shorter biological half-life. In addition, the truncated protein may have unusual amino acids at the COOH end, possibly producing an immune response to hCG, useful in a vaccination strategy.

C. Human c-myc (GenBank J00120)

c-myc is a proto-oncogene which regulates cell growth and differentiation and is involved in the processes of vascular remodeling, smooth muscle cell proliferation, extracellular matrix synthesis, and apoptosis. Aberrant expression of c-myc is frequently observed in human cancer. Aberrant, constitutive or overexpression of c-myc has been associated with a number of human cancers including lung cancer, colorectal cancer, breast cancer, bladder cancer, leukemia, lung cancer, etc. It has also been demonstrated that inhibition of c-myc reduces the incidence and severity of restenosis.

The c-myc protein has a DNA binding domain in the amine-terminal portion of the sequence and a protein-protein interacting domain in the carboxy-terminal portion. It is known that c-myc binds with Max in the carboxy domain to form a heterodimer that can bind to a DNA sequence known as an E-Box (5'-CACGTG-3'). When myc:max binds in this manner, the phenotype is growth stimulatory and can lead to apoptosis.

If myc concentration is low, then max forms homodimers which do not transactivate. If the mad protein is induced, then max binds mad to form mad:max heterodimers, which tend to induce differentiation and are anti-apoptotic.

Hence, simply inhibiting myc tends to result in the mad:max phenotype, which is anti-apoptotic. However, if the DNA binding (amine-terminal) domain of c-myc is inhibited, while leaving the protein-protein binding (carboxy-terminal) domain intact, the result is a dominant negative protein capable of binding max but not capable of transactivation. The favorable phenotype would be the loss of growth stimulatory actions, but the compensatory anti-apoptotic actions of mad:max would not dominate, as max protein can still bind to the myc COOH domain.

Inhibition of the amine-terminal domain is achieved by appropriate design of an antisense compound to direct alteration of splicing. Cryptic (alternate) SA sites found downstream include:

4547 Possible candidate; the next AUG, at 4554, is out of frame and would thus produce unrelated ("nonsense") protein. (Could be blocked by oligos targeted further downstream than SEQ ID NO: 13)

4578 Not a good SA candidate, due to few pyrimidines upstream

4617 A good SA candidate; next downstream AUG is at 4821, which is in frame with normal AUG at 4521

As described above, a morpholino oligomer (PMO) having a sequence complementary to bases 4515 to 4534 of the human c-myc mRNA sequence (Genbank Accession No. J00120), ten bases downstream of the splice acceptor site AG at 4504-5 (SEQ ID NO. 25, 5'-ACG TTG AGG GGC ATC GTC GC-3'), was found to prevent appropriate splicing at this site and the use of the normal AUG translation start site at 4521. Analysis of the mRNA produced indicated use of the 4617 site indicated above. Translation starting at the AUG at 4821, 300 bases downstream of the normal AUG, produces a protein having a 100 amino acid deletion at the N-terminus (as also reported by Giles et al.) Use of antibodies to the COOH end of myc revealed this protein, as well as substantially smaller proteins, from cells treated with the antisense oligomer. These N-terminal truncated proteins are expected to bind max but will not bind DNA.

These results, combined with examination of primer-amplified mRNAs, demonstrated the use of the 4617 cryptic splice site, as well as other cryptic sites further downstream.

As noted above, PMO oligomers targeted to the region from −44 upstream of the SA to +36 downstream (ds) from the SA showed evidence of interference with splicing in rat c-myc. Assuming an oligomer length of about 20 bases, the following antisense sequences could thus be utilized for targeting of human c-myc:

TABLE 2

| Antisense Sequence | Bases ds of SA site (5' end of sequence) | SEQ ID NO: |
| --- | --- | --- |
| 5'-GGCATCGTCGCGGGAGGCTG-3' | 1 | 16 |
| 5'-GGGCATCGTCGCGGGAGGCT-3' | 2 | 17 |
| 5'-GGGGCATCGTCGCGGGAGGC-3' | 3 | 18 |
| 5'-AGGGGCATCGTCGCGGGAGG-3' | 4 | 19 |
| 5'-GAGGGGCATCGTCGCGGGAG-3' | 5 | 20 |
| 5'-TGAGGGGCATCGTCGCGGGA-3' | 6 | 21 |

TABLE 2-continued

| Antisense Sequence | Bases ds of SA site (5' end of sequence) | SEQ ID NO: |
|---|---|---|
| 5'-TTGAGGGGCATCGTCGCGGG-3' | 7 | 22 |
| 5'-GTTGAGGGGCATCGTCGCGG-3' | 8 | 23 |
| 5'-CGTTGAGGGGCATCGTCGCG-3' | 9 | 24 |
| 5'-ACGTTGAGGGGCATCGTCGC-3' | 10 | 25 |
| 5'-AACGTTGAGGGGCATCGTCG-3' | 11 | 26 |
| 5'-TAACGTTGAGGGGCATCGTC-3' | 12 | 27 |
| 5'-CTAACGTTGAGGGGCATCGT-3' | 13 | 28 |
| 5'-GCTAACGTTGAGGGGCATCG-3' | 14 | 29 |
| 5'-AGCTAACGTTGAGGGGCATC-3' | 15 | 30 |
| 5'-AAGCTAACGTTGAGGGGCAT-3' | 16 | 31 |
| 5'-GAAGCTAACGTTGAGGGGCA-3' | 17 | 32 |

The protein-protein binding (carboxy terminal) domain of myc could also be altered, as follows. An oligomer with the antisense sequence 5'-TCC TCA TCT TCT TGT TCC TC-3' (SEQ ID NO: 33) targets base 6656, downstream of the splice acceptor at base 6654-5. Likely downstream cryptic SA sites are at bases 6704, 6710, and 6729 (AG at 6702-3; CAG at 6707-09; CAG at 6726-8; A branch point at 6684; pyrimidine-rich region starting at 6690). Of these, the first two are out of frame and the third is in frame. Use of the third site would be expected to produce a deletion of 75 base pairs from the mRNA, resulting in a 25 amino acid deletion in the protein-protein binding domain of the myc protein. This protein would be the converse dominant negative, as DNA binding may be possible but no myc:max transactivation is likely. The function of myc would be lost, but the mad:max heterodimers would be favored, so that the phenotype of differentiation and anti-apoptosis would be observed.

As noted above, oligomers targeted progressively farther downstream, relative to SEQ ID NO: 33, could also be used. This includes, for example, oligomers having a length of about 18-20 contiguous nucleotides selected from the sequence 5'-AAC AAC ATC GAT TTC TTC CTC ATC TTC TTG TTC CTC-3' (SEQ ID NO: 34; complementary to bases 6656-91 of the sequence given in Genbank Acc. No. J00120). In accordance with the invention, an oligomer targeted far enough downstream to inhibit splicing at the first two cryptic sites noted above could be effective to promote splicing at the third cryptic site.

D. Human p53 (GenBank X54156)

Like c-myc, p53 has a non-coding exon 1, a large intron 1 and an AUG start codon near the SA site of exon 2. An oligomer targeted, for example, to the region having its 5' end at base 11691, three bases downstream of the SA site (5'-CCC GGA AGG CAG TCT GGC-3'; SEQ ID NO: 35) is expected to interfere with translation at the AUG initiation site as well as the normal splicing of exon 2. As described for c-myc above, other suitable oligomers include those targeted one or two bases downstream of the SA site, or targeted progressively further downstream, e.g. starting at base 11691, 11692, etc., and targeting some portion of the region between base 11689 (the first base of the normal exon 2) and about base 11725. This includes, for example, oligomers having a length of about 18-20 contiguous nucleotides selected from the sequence 5'-TCC TCC ATG GCA GTG ACC CGG AAG GCA GTC TGG CTG-3' (SEQ ID NO: 36; complementary to bases 11689-11724 of the sequence given in Genbank Acc. No. X54156).

Cryptic SA sites are available at base 11761 (AG at 11759-60) and at base 11765 (CAG at 11762-4) (A branch point at 11736; pyrimidine run at 11750-57). The next AUG, at base 11782, is out of frame, which will result in nonsense proteins. Alternatively, initiation may begin in exon 3, producing truncated p53-type proteins without the p53 amino terminus.

The following is an example in which targeting of the splice acceptor is especially advantageous.

E. Human Abl (GenBank AJ131466)

Since the bcr gene breaks and fuses to abl, forming the bcr-abl fusion protein, in chronic myeloid leukemia, it is a target of antisense inhibition. With respect to abl, fusion can occur at various locations; i.e. there are breaks after exon 1, 2 and 3 of bcr that fuse to Exon 2 of abl. However, by targeting the splice acceptor of abl, only one oligomer is required for treatment of all CML patients.

The bcr-abl fusion point is at the junction of bases 373-374. Therefore, the abl splice acceptor could be targeted by the following sequence, three bases downstream of this junction: 5'-CTA CTG GCC GCT GAA GGG C-3' (SEQ ID NO: 37).

Again, other oligomers targeting the region between the splice junction and about 35-40 bases downstream of the splice junction could also be used. This includes, for example, oligomers having a length of about 18-20 contiguous nucleotides selected from the sequence 5'-GCT CAA AGT CAG ATG CTA CTG GCC GCT GAA GGG CTT-3' (SEQ ID NO: 38; complementary to bases 374-409 of the sequence given in Genbank Acc. No. AJ131466). Possible cryptic splice sites (both out of frame) include CAG motifs at 468-70, with an upstream pyrimidine region at 453-459 and an A branch point at 421, and at 516-518, with an upstream pyrimidine region at 507-510 and an A branch point at 485.

F. HIV-1 (GenBank L39106)

This example illustrates a situation in which the method of the invention provides particular advantages; that is, where both a target virus and the host (human) express a gene with the same mRNA sequences. The protein products are important to the function of both virus and host but serve different functions.

An mRNA sequence of HIV-1 rev, which encodes a protein critical for viral replication (see e.g. H Mitsuya et al., *Science* 249:1533-1543, 1990), was found to also occur in the host, leading to toxic effects when this sequence was inhibited by antisense. Specifically, a phosphorothioate oligomer having the sequence 5'-TCG TCG GTC TCT CCG CTT CTT CTT GCC-3' (SEQ ID NO: 39) was used to inhibit HIV-1 rev (Matsukura et al., *PNAS USA* 86:4244-4248, 1989). This region of rev is highly conserved in HIV; accordingly, it was targeted so that a large variety of viral isolates might be inhibited.

However, the preclinical development of this 27-mer was ended when 2 of 3 Rhesus monkeys treated by continuous infusion died of what appeared to be opportunistic infections. An excessive endotoxin burden was suspected, so the experiment was repeated, with care taken to remove endotoxin. However, two cynamologous monkeys also died on days 8 and 9 of the continuous infusion in the repeat study. As endotoxin was effectively removed from consideration, immunosuppression was suggested as the cause. The white blood cell (WBC) count in the three Rhesus monkeys was 9.5±0.7 prior to infusion with the antisense phosphorothioate to HIV-rev, and fell to 6.9±0.6 during the infusion. There was no associated change in RBC or hematocrit. Further, surface marker studies for cells involved in immune response were influenced: CD2 was reduced from 88 to 76, CD8 fell from 45 to 36, and CD20 rose from 14 to 18.

A homologous region to HIV-rev observed in the genomes of humans and monkeys was reported in *Virology* 66:2170-2179 (1992), thus accounting for these toxic effects.

According to the present method, an alternative sequence could be selected which is less likely to interfere with host processes. In accordance with the present invention, HIV-rev could be suppressed as follows.

The protein is encoded by two exons: exon 1, 5493 . . . 5568, 76 bases; and exon 2, 7885 . . . 8180, 296 bases; 124 amino acids total (GenBank L39106). An antisense, RNAse H-incompetent oligomer targeted to the region between the splice junction (i.e. the first base of normal exon 2) and about 35-40 bases downstream of the splice junction is expected to interfere with splicing of the pre-mRNA. As specified above, the 5' end of the targeted region is preferably 1 to about 25 bases downstream of the splice junction. An example of such an oligomer is a PMO targeted to base pairs 7885-7904, having the sequence 5'-CTC TGG TGG TGG GTA AGG GT-3' (SEQ ID NO: 40). Other candidates include oligomers having a length of about 18-20 contiguous nucleotides selected from the sequence 5'-CGG GTC TGT CGG GTT CCC TCT GGT GGT GGG TAA GGG T-3' (SEQ ID NO: 41; complementary to bases 7885-7921 of the sequence given in Genbank Acc. No. L39106).

The most likely site for a cryptic splice acceptor is at base 7975, where an AG sequence is preceded by multiple pyrimidines over 10 bases upstream from the AG. If this cryptic splice-acceptor is utilized, a deletion of 90 bases, or 30 amino acids, will result. This deletion will interfere with effective viral rev gene function.

VI. Analysis of Effects of Splice Acceptor Targeting

The effectiveness of a particular antisense sequence in producing splice variant mRNA may be determined by known analytical methods. For example, the presence or absence of the encoded, full-length protein and of truncated or other variant proteins can be monitored by standard techniques such as ELISA or Western blotting. Antibodies targeted to specific regions of the proteins, e.g. to the carboxy or amino terminus, can also be employed.

mRNA structure can be analyzed to evaluate antisense oligomer induced missplicing. The recovery of nuclear RNA is essential to observe intron-containing hnRNA, as the nucleus is the site of intron removal. Preparation of nuclear RNA is described in books such as "Molecular Cloning, A Laboratory Manual" (T. Maniatis, E. F. Fritsch and J. Sambrook, eds., Cold Spring Harbor Press) or "Current Protocols in Molecular Biology" (F. M. Ausubel et al., eds., John Wiley & Sons, Inc.). The analysis of hnRNA is best done by either Northern blot or 51 Mapping. The presence of particular splice variant mature mRNAs can be determined by carrying out PCR amplification using selected primer pairs having sequences predicted to occur in a specific splice variant (or normal) processed mRNA. One primer is positioned in the SD (splice donor) exon upstream of the splice site, and the second is positioned in the SA (splice acceptor) exon, downstream of the splice site. Since the oligomer interferes with the SA site, the downstream primer should be more than 50 bases downstream from the SA splice site. Analysis of the PCR reactions on agarose gels stained with ethidium bromide will reveal amplified bands which are smaller in size than bands observed from untreated control cells, as evidence of blocking of the SA site by the oligomer.

VII. Advantages of the Method

The present invention demonstrates that inhibition or alteration of protein expression can be achieved by antisense targeting of a region downstream of a splice acceptor, in the coding region of a pre-mRNA, using a non-RNAse competent oligomer. The present compositions and methods have several advantages over prior art methods of antisense inhibition, in which the targeting antisense compound spans and hybridizes to a splice acceptor sequence (e.g. Giles, cited above; Kole and Dominski, U.S. Pat. No. 5,665,593).

One such advantage is that exon sequences tend to much more highly conserved among species than intron sequences. This allows for greater predictability in testing such methods on animal models.

In addition, greater flexibility is allowed in selecting a sequence for targeting, as the oligomer is not required to actually bind to a precise site such as a splice acceptor junction or an AUG start codon. The present invention thus increases the range of sequences which may be successfully targeted in an antisense application. Such flexibility can be advantageous in avoiding undesirable side reactions, such as caused by inadvertent targeting of non-target proteins in a subject, or targeting of host proteins when attacking an infectious agent such as a virus or bacterium. This is demonstrated in Example F, above.

In the present strategy, in contrast to methods which target the splice junction directly, various regions of the exon downstream of the SA site may be blocked. This opens the possibility of producing different variant proteins, by directing splicing to different cryptic splice sites downstream of the normal SA. As described above, certain variant proteins, such as dominant negative proteins, can have unique advantages. Accordingly, the antisense could be designed to promote splicing at a particular cryptic splice site, which would give rise to the desired variant protein, over others. For example, a less desirable cryptic splice site close to the normal SA site could be hindered in favor of a site further downstream.

Further benefits of flexibility of design may include convenience of synthesis or enhanced binding affinity. In addition, by using the present strategy of targeting fully within the exon, the target RNA can be identified by the antisense oligomer in either the nucleus or the cytoplasm, which can be advantageous for purposes of analysis.

VIII. Treatment Methods

In a related aspect, the invention includes a method of treating or preventing a disease state by inhibiting or altering expression of a target protein. Such disease states include viral, bacterial or fungal infections, cancerous tumors, and other conditions characterized by cellular proliferation, such as restenosis, hyperproliferative skin disorders, or inflammation. Proteins targeted, as noted above, include transcription factors, which include many oncogenes, receptor proteins, matrix proteins, and viral proteins. Inhibition of such proteins generally results in disruption of the cell cycle, viral replication, or other critical functions.

The method is carried out by administering to the subject an antisense oligomer 12 to 25 nucleotides in length and having (i) a base sequence complementary to a target region of a selected preprocessed mRNA coding for the target protein, where the 5' end of the target region is 1-25 bases downstream, and preferably 2-15 bases downstream, of a normal splice acceptor site in the preprocessed mRNA, and (ii) an uncharged morpholino backbone, preferably a phosphorodiamidate backbone as shown in FIG. 3, where X, Y, and Z are as defined above. Preferably, the compound also contains a moiety that enhances the solubility of the compound, preferably to a solubility in aqueous medium of between 25-50 mgs/ml or greater. An example is a polyethylene glycol (PEG) chain.

In general, the method comprises administering to a subject, in a suitable pharmaceutical carrier, an amount of the antisense agent effective to interfere with splicing at the normal splice acceptor site, and thus suppress normal expression of the protein. In a preferred embodiment, the method results in expression of a dominant negative variant of the protein. In one aspect of the method, the subject is a human subject.

Effective delivery of the antisense oligomer to the target mRNA is an important aspect of the method. PMOs have been shown to enter cells efficiently (see e.g. J Summerton et al., *Antisense Nucleic Acid Drug Dev.* 7:63-70, 1997, and co-owned U.S. provisional application 60/117,846). For use in antiviral treatment, various systemic routes of delivery, including oral and parenteral routes, e.g., intravenous, subcutaneous, intraperitoneal, and intramuscular, as well as inhalation, transdermal and topical delivery, can be used.

Typically, one or more doses of antisense oligomer are administered, generally at regular intervals for a period of about one to two weeks. Preferred doses for oral administration are from about 1 mg oligomer/patient to about 25 mg oligomer/patient (based on a weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg). Dosages will vary in accordance with such factors as the age, health, sex, size and weight of the patient, the route of administration, and the efficacy of the oligonucleotide agent with respect to the particular disease state. For treatment of infectious agents, a preferred dosage is typically that which is necessary to attain a concentration in the blood of from about 0.01 to about 1 and more preferably about 200-400 nM antisense oligomer. This concentration can be achieved in a variety of ways; doses of between about 0.05 and about 0.2 mg/kg/hour by continuous IV infusion have been found to be acceptable. Greater or lesser amounts of oligonucleotide may be administered as required.

For treatment of hyperproliferative skin disorders, topical administration is indicated. In treatment of restenosis, delivery of the antisense oligomer to the affected cells, that is, to the site of arterial injury, is recommended. Delivery methods known in the field, such as those described in co-owned and copending U.S. application Ser. No. 09/493,427, can be used to deliver the oligomer to the site of angioplasty in a patient. Preferably, the oligomer is delivered concurrent with the angioplasty procedure. For an adult human, a recommended dosage is in the range of 1-25 μmol of antisense oligomer, and preferably 2-15 μmol. With respect to the surface area of tissue to be treated, an effective dose is typically in the range of 30 to 3000 μg oligomer per $cm^2$ of vessel wall, and more preferably about 300 to 1500 μg/$cm^2$. The patient may also be given the composition on a periodic basis after angioplasty, at a dosage level sufficient to further inhibit restenosis.

An effective in vivo treatment regimen using the antisense oligonucleotides of the invention will vary according to the frequency and route of administration, as well as the condition of the subject under treatment. Optimum dosages for a given route can be determined by routine experimentation according to methods known in the art. Such in vivo therapy is generally monitored by tests appropriate to the particular type of ailment being treated, and a corresponding adjustment in the dose or treatment regimen can be made in order to achieve an optimal therapeutic outcome.

Entry of a morpholino oligomer into cells and binding to its target RNA sequence can be verified by techniques set forth in co-owned U.S. provisional application 60/117,846, which is incorporated herein by reference. A morpholino antisense compound of the type disclosed herein, when administered in vivo, can be detected in the urine of the receiving subject in a heteroduplex form consisting of the antisense compound and its RNA complement. This verifies that the antisense compound has been taken up by the target tissue and allows the practitioner to monitor the effectiveness of the treatment method, e.g. the effectiveness of various modes of administration, and dosages giving maximal or near-maximal levels of heteroduplex in the urine.

IX. Formulations

A morpholino antisense oligonucleotide composition may be administered in any convenient physiologically acceptable vehicle. Examples of standard pharmaceutically accepted carriers include saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In general, in addition to the active compounds, the pharmaceutical compositions of the invention may contain suitable excipients and auxiliaries which facilitate processing of the active compounds into preparations which can be used pharmaceutically. Suitable excipients include fillers such as sugars, for example, lactose, sucrose, mannitol or sorbitol, cellulose preparations, calcium phosphates, and binders such as starch, gelatin, methyl cellulose, hydroxypropyl methylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, alginic acid, or a salt thereof. Auxiliaries include flow-regulating agents and lubricants, for example, silica, talc, stearic acid or salts thereof, and/or polyethylene glycol.

For oral administration, dragee cores may be provided with suitable coatings which are resistant to gastric juices. In order to produce coatings resistant to gastric juices, solutions of suitable cellulose preparations, such as acetylcellulose phthalate or hydroxypropylmethyl-cellulose phthalate, are used. Concentrated sugar solutions may be used, which may optionally contain gum arabic, talc, polyvinylpyrrolidone, polyethyleneglycol, and/or titanium dioxide, lacquer solutions, and suitable organic solvents or solvent mixtures.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Pharmaceutical preparations which can be used rectally include, for example, suppositories, which consist of a combination of the active compounds with a suppository base. Suitable suppository bases include natural or synthetic triglycerides, paraffin hydrocarbons, polyethylene glycols, or higher alkanols. In addition, it is possible to use gelatin rectal capsules which consist of a combination of the active compounds with a base. Possible base materials include liquid triglycerides, polyethylene glycols, or paraffin hydrocarbons.

Suitable liquid formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, such as sodium carboxymethyl cellulose, sorbitol, and/or dextran. The suspension may also contain stabilizers.

In addition to administration with conventional carriers, the active ingredients may be administered by a variety of specialized delivery techniques. For example, the compounds of the present invention may be administered encapsulated in liposomes. (See, e.g., Williams, S. A., *Leukemia* 10(12):1980-1989, 1996; Lappalainen et al., *Antiviral Res.* 23:119, 1994; Uhlmann et al., "Antisense Oligonucleotides: A New Therapeutic Principle", in *Chemical Reviews*, Volume 90, No. 4, pp 544-584, 1990; Gregoriadis, G., Chapter 14, "Liposomes", in *Drug Carriers in Biology and Medicine*, pp 287-341, Academic Press, 1979.) The active ingredient, depending upon its solubility, may be present both in the aqueous phase and in the lipidic layer(s), or in what is generally termed a liposomic suspension. The lipidic layer generally comprises phospholipids, such as lecithin or sphingomyelin, steroids such as cholesterol, ionic surfactants such as diacetylphosphate, stearylamine, or phosphatidic acid, and/or other hydrophobic materials. The diameters of the liposomes generally range from about 15 nm to about 5 microns.

Hydrogels may also be used as vehicles for antisense oligomer administration, for example, as described in WO 93/01286. Alternatively, the oligonucleotides may be administered in microspheres or microparticles. (See, e.g., Wu G Y and Wu C H, *J. Biol. Chem.* 262:4429-4432, 1987.) Such vehicles are particularly suited for topical administration or in treating restenosis.

Transdermal delivery of antisense oligomers may be accomplished by use of a pharmaceutically acceptable carrier adapted for topical administration. One example of morpholino oligomer delivery is described in PCT patent application WO 97/40854. Other sustained release compositions are also contemplated within the scope of this application. These may include semipermeable polymeric matrices in the form of shaped articles such as films or microcapsules.

Methods for preparing such dosage forms are known or will be apparent to those skilled in the art; for example, see *Remington's Pharmaceutical Sciences* (19th Ed., Williams & Wilkins, 1995). The pharmaceutical preparations are manufactured according to procedures well known in the art. For example, they may be made by means of conventional mixing, granulating, dragee-making, dissolving, or lyophilizing processes. The process to be used will depend ultimately on the physical properties of the active ingredient used.

Materials and Methods

Oligomers

PMO's were synthesized at AVI BioPharma by methods described, for example, in Summerton and Weller, *Antisense & Nucleic Acid Drug Dev.* 7:187-95, 1993; U.S. Pat. No. 5,185,444, 1997. The oligomers were purified by ion exchange chromatography and analyzed for purity by high-performance liquid chromatography (HPLC) and mass spectrometry. The amount of full-length product was generally >90%. Before use, they were prepared as concentrated stock solutions with distilled water and stored at 4° C.

Cell Culture

Cells were obtained from the American Type Culture Collection (ATCC, Rockville, Md.) or were derived in this laboratory. They were cultured in a 1:1 mixture of Dulbecco's modified Eagle's medium (DMEM) and Ham's nutrient mixture F-12 supplemented with glutamine (2 mM), streptomycin (100 ug/ml), and penicillin (100 U/ml). Dialyzed fetal bovine serum (FBS) was purchased from either Sigma (St. Louis, Mo.) or Hyclone (Ogden, Utah). WI-38 and HeLa cells were cultured in 10% serum and NRK cells were cultured in 4% serum.

Recombinant Plasmids and Cell Lines

The human myc genomic clone pHSR-1 was a deposit from M. Bishop to the ATCC. The 2.2-kilobase (kb) 5'-end was adapted for cloning into a luciferase vector by PCR using appropriate restriction sites incorporated into the primers (Scharf, 1990). The luciferase vector was adapted from one supplied by Clontech Inc. (Palo Alto, Calif.) to allow N-terminal fusion proteins with insect luciferase. Plasmids were introduced into HeLa cells using the Lipofectin protocol and reagent from Life Science Technologies (Gaithersburg, Md.) using the neomycin gene/Geneticin selection procedure (F Colbere-Garapin et al., *J. Mol Biol.* 150:1-14, 1981). The rabbit α-globin-luciferase construct-containing cell line has been described (M Partridge et al., *Antisense & Nucleic Acid Drug Dev.* 6:169-75, 1996).

[$^3$H] Thymidine Incorporation Assay

Cells were trypsinized, counted, and plated at 400,000 cells/2 ml/well into 6-well dishes. On day 2, PMO antisense agents were added to the desired concentration, and the cells were scrape loaded (P L McNeil et al., *J. Cell Biol.* 98:1556-64, 1984; Partridge et al., cited above) with a rubber policeman using a gentle sweeping motion. The cell suspension was pipetted once to partly disaggregate any clumps formed, and 1 ml was transferred to a 24-well dish containing an additional 1 ml/well of fresh medium. For NRK cells, on day 4, 1 µCi of [$^3$H]thymidine (DuPont, NEN, Wilmington, Del.) (NET-027) was added per well, and 6 hours later, the cells were washed twice with phosphate-buffered saline (PBS), precipitated with 5% trichloroacetic acid, washed a further two times with PBS, solubilized with 0.2 N NaOH/0.1% SDS, and the amount of radioactivity was incorporated into DNA quantitated in a scintillation counter. The quantitation procedure was identical for WI-38 cells except that the incubation period for incorporation was 15 hours. In general, each agent or concentration was assayed in duplicate, and the values were averaged. The duplicates were usually within 10% of each other.

Luciferase Assay

The myc-luciferase HeLa cells were scrape loaded in a manner similar to the normal fibroblasts with the following changes. One million cells were plated into 6-well dishes, and on day 2 the entire 2 ml volume was transferred to another 6-well dish. Thirty hours later, the cells were collected and assayed for luciferase light production as described (Partridge et al.; 1996; Summerton et al., 1997; cited above).

Cell Cycle Analysis

Cells were analyzed for cell cycle stage by flow cytometry. The cells were scrape loaded as described, and two wells were combined and replated in 10-cm dishes to obtain enough cells for analysis by fluorescence-activated cell sorting (FACS). Two days later, the cells were trypsinized, washed with PBS and resuspended in cold 80% ethanol for at least 2 hours. Following the fixation step, the cells were collected by centrifugation and stained with the DNA fluorochrome propidium iodide (Telford et al., cited above). The ethanol-treated pellet was resuspended in 1 ml of 1 mM EDTA, 50 µg/ml propidium iodide, 1 µl/ml Triton X-100, and 10 µg/ml RNase A. After at least 1 hour at ambient temperature, the cell suspension was analyzed using a Coulter Epic XL-MCL flow cytometer (Coulter Electronics, Hialeah, Fla.) with an exciting wavelength of 488 nm. Data were analyzed using Phoenix Systems (San Jose, Calif.) multicycle program software.

mRNA Reverse Transcriptase-Polymerase Chain Reaction (RT-PCR) Analysis

To examine the effects of Morpholino oligomers on myc RNA splicing, HeLa cells were plated in 6-well dishes at 1 million cells/well. The next day, oligomers at 20 µM final concentration were added to the medium and scrape loaded into the cells as detailed previously. Twenty-four hours later, the loaded cells were harvested by trypsinization and RNA prepared. Two wells were combined for each sample. Cytoplasmic (mature) RNA was extracted from the cell pellet by a Triton X-100 lysis procedure using a Qiagen Rneasy Mini Kit (Chartsworth, Calif.) following the directions for "isolation of RNA from the cytoplasm of animal cells." The RNA was eluted in 30 µl of water with a yield of about 10-20 µg.

Six microliters of RNA (2-3 µg) was reverse transcribed in a final 20 µl reaction mixture with 1×PCR buffer (10 mM Tris, pH 8.3, 50 mM KCl, 1.5 mM $MgCl_2$) (Perkin-Elmer, Norwalk, Conn.) 1 mM of each deoxynucleotide triphosphate, 0.75 µg 9-mer random primers, and 250 U Moloney murine leukemia virus (MmuLV) RT (New England Bio-Labs, Beverly, Mass.). After addition of enzyme, the reactions were incubated for 10 minutes at 25° C., following by 30 minutes at 42° C., and 4 minutes to denature the polymerase at 94° C.

Exon 1-exon 2 PCR was performed using a two-step nested PCR procedure. Step 1 primers had the sequences 5'-CGG GCA CTT TGC ACT GAA ACT TAC AAC ACC (SEQ ID NO: 51) and 5'-GGT CGC AGA TGA AAC TCT GGT T (SEQ ID NO: 52). One microgram of each of the primers was added to the 20 µl RT reaction, and the volume was adjusted to 100 µl with 1×PCR buffer. Four units of Amplitaq (Perkin-Elmer) Taq polymerase were added, and 30 cycles were performed with steps of 94° C. for 30 seconds, 62° C. for 30 seconds, and 72° C. for 40 seconds. Step 2 used primer sequences of 5'-CTC CTT GCA GCT GCT TAG ACG CTG G (SEQ ID NO: 53) and 5'-GAA GGG TGT GAC CGC AAC GTA GGA G (SEQ ID NO: 54). The step 1 reaction mixture (4 µl) was added to 96 µl of 1×PCR buffer with 200 nM of each triphosphate and 1 µg of each primer. Step 2 PCR conditions were 30 cycles of 94° C. for 30 seconds, 68° C. for 40 seconds, and 74° C. for 30 seconds. Aliquots were then analyzed by agarose gel electrophoresis.

Although the invention has been described with reference to specific methods and embodiments, it will be appreciated that various modifications and changes may be made without departing from the invention.

Sequence Table

| SEQ ID NO | Sequence (5' → 3') | Target† | Genbank Acc. No. | Location |
|---|---|---|---|---|
| 1 | CTGTGCTTAC/CGGGTTTTCCACCTCCC | Rat c-myc (SD) | Y00396 | 2553-79 |
| 2 | ATCGTCGTGACTGT/CTGTTGGAGGG | Rat c-myc (SA) | | 4140-64 |
| 3 | GCTCACGTTGAGGGGCATCG | Rat c-myc (ds of SA) | | 4161-80 |
| 4 | GGTCACTCAC/CGGTAGAGAA | Rat CYP3A2 (SD) | X62087 | 1155-74 |
| 5 | GGGTTCCAAGT/CTATAAAGG | Rat CYP3A2 (SA) | | 1526-45 |
| 6* | TGTGTCTTTTCCAG | Human androgen receptor exon 2 | M35845 | 31-44 |
| 7* | TTTGGAGACTGCCAGGGACCATG | Human androgen receptor exon 2 | | 45-67 |
| 8 | CATGGTCCCTGGCAGTCTCC | Human androgen receptor exon 2 | | 48-67 |
| 9 | TCAATGGGCAAAACATGGTCCCTGGCAGTCTCCAAA | Human androgen receptor exon 2 | | 45-80 |
| 10* | TTTGTGTTCTCCCAG | Human androgen receptor exon 3 | M35836 | 28-43 |
| 11* | GGAAACAGAAGTACCTGTGCGCC | Human androgen receptor exon 3 | | 44-66 |

Sequence Table

| SEQ ID NO | Sequence (5' → 3') | Target† | Genbank Acc. No. | Location |
|---|---|---|---|---|
| 12 | GGCGCACAGGTACTTCTG | Human androgen receptor exon 3 | | 49-66 |
| 13 | AATCATTTCTGCTGGCGCACAGGTACTTCTGTTTCC | Human androgen receptor exon 3 | | 44-79 |
| 14 | CCCCTGCAGCACGCGGGT | Human HCG-β subunit | X00266 | 1321-38 |
| 15 | GAGGCAGGGCCGGCAGGACCCCCTGCAGCACGCGGGT | " | | 1321-57 |
| 16 | GGCATCGTCGCGGGAGGCTG | Human c-myc | J00120 | 4506-25 |
| 17 | GGGCATCGTCGCGGGAGGCT | " | | 4507-26 |
| 18 | GGGGCATCGTCGCGGGAGGC | " | | 4508-27 |
| 19 | AGGGGCATCGTCGCGGGAGG | " | | 4509-28 |
| 20 | GAGGGGCATCGTCGCGGGAG | " | | 4510-29 |
| 21 | TGAGGGGCATCGTCGCGGGA | " | | 4511-30 |
| 22 | TTGAGGGGCATCGTCGCGGG | " | | 4512-31 |
| 23 | GTTGAGGGGCATCGTCGCGG | " | | 4513-32 |
| 24 | CGTTGAGGGGCATCGTCGCG | " | | 4514-33 |
| 25 | ACGTTGAGGGGCATCGTCGC | " | | 4515-34 |
| 26 | AACGTTGAGGGGCATCGTCG | " | | 4516-35 |
| 27 | TAACGTTGAGGGGCATCGTC | " | | 4517-36 |
| 28 | CTAACGTTGAGGGGCATCGT | " | | 4518-37 |
| 29 | GCTAACGTTGAGGGGCATCG | " | | 4519-38 |
| 30 | AGCTAACGTTGAGGGGCATC | " | | 4520-39 |
| 31 | AAGCTAACGTTGAGGGGCAT | " | | 4521-40 |
| 32 | GAAGCTAACGTTGAGGGGCA | " | | 4522-41 |
| 33 | TCCTCATCTTCTTGTTCCTC | " | | 6656-75 |
| 34 | AACAACATCGATTTCTTCCTCATCTTCTTGTTCCTC | " | | 6656-91 |
| 35 | CCCGGAAGGCAGTCTGGC | Human p53 | X54156 | 11691-708 |
| 36 | TCCTCCATGGCAGTGACCCGGAAGGCAGTCTGGCTG | " | | 11689-724 |
| 37 | CTACTGGCCGCTGAAGGGC | Human abl (ds of bcr-abl fusion point) | AJ131466 | 376-94 |
| 38 | GCTCAAAGTCAGATGCTACTGGCCGCTGAAGGGCTT | Human abl (ds of bcr-abl fusion point) | | 374-409 |
| 39 | TCGTCGGTCTCTCCGCTTCTTCTTGCC | HIV-1 rev (prior art) | U69590 | 5517-43 |
| 40 | CTCTGGTGGTGGGTAAGGGT | HIV-1 rev | L39106 | 7885-7904 |
| 41 | CGGGTCTGTCGGGTTCCCTCTGGTGGTGGGTAAGGGT | " | | 7885-7921 |
| 42 | GGGGCAUCGUCGUGACUGU/CUGUUGGAGGG | Rat c-myc (SA) | Y00396 | 4140-69 |
| 43 | CGUCGUGACUGU/CUGUUGGAGG | " | Y00396 | 4141-62 |
| 44 | CGTCGTGACTGT/CTGTTGGAGG | " | Y00396 | 4141-62 |
| 45 | GGCAUCGUCGCGGGAGGCUG/CUGGAGCG | Human c-myc (SA) | J00120 | 4498-4505 |
| 46 | CCGCGACAUAGGACGGAGAGCAGAGCCC | Rat c-myc | Y00396 | 4364-91 |

Sequence Table

| SEQ ID NO | Sequence (5' → 3') | Target† | Genbank Acc. No. | Location |
|---|---|---|---|---|
| 47 | ACTGTGAGGGCGATCGCTGC (scrambled) | derived from SEQ ID NO: 25 | | |
| 48 | ACGATGAGTGGCATAGTCGC (3 mismatches) | derived from SEQ ID NO: 25 | | |
| 49 | CTCCGCAATGCTGAAAGGTG | Rat BCL-2 (cntrl) | | |
| 50 | GGCGUGCCUCAAACAUGGUGGCGG | Rat PCNA-1 (cntrl) | | |
| 51 | CGGGCACTTTGCACTGAAACTTACAACACC | primer sequence | | |
| 52 | GGTCGCAGATGAAACTCTGGTT | " | | |
| 53 | CTCCTTGCAGCTGCTTAGACGCTGG | " | | |
| 54 | GAAGGGTGTGACCGCAACGTAGGAG | " | | |

*native sequence, not antisense
†unless otherwise indicated, antisense target is downstream (ds) of splice acceptor (SA) junction; SD = splice donor junction

---

It is claimed:

1. A pharmaceutical composition comprising an oligomer of 8 to 40 morpholino subunits connected by phosphorous-containing intersubunit linkages, wherein the 5' terminal morpholino subunit comprises a group of the formula:

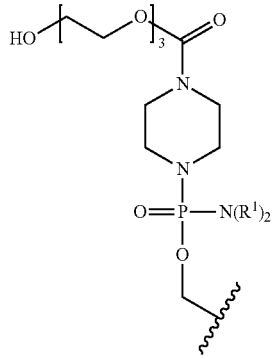

or a pharmaceutically acceptable salt thereof, wherein each $R^1$ is independently a $C_1$-$C_6$ alkyl, and a pharmaceutically acceptable carrier.

2. The pharmaceutical composition of claim 1, wherein the 5' terminal morpholino subunit of the oligomer is of a formula:

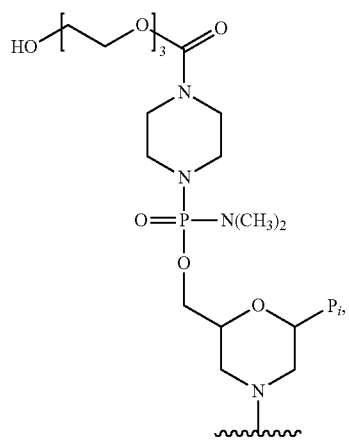

wherein each $P_i$ is independently a purine or pyrimidine base-pairing moiety.

3. The pharmaceutical composition of claim 1, wherein the oligomer is of a formula:

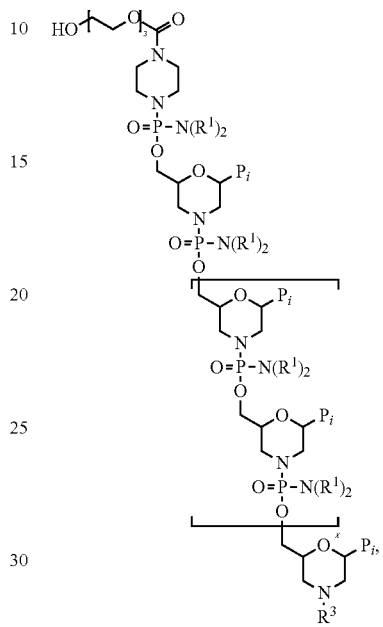

or a pharmaceutically acceptable salt thereof,
wherein:
 each $R^1$ is independently a $C_1$-$C_6$ alkyl;
 each $P_i$ is independently a purine or pyrimidine base-pairing moiety;
 X is an integer from 3 to 19; and
 $R^3$ is H.

4. The pharmaceutical composition of claim 3, wherein each $R^1$ is independently selected from methyl, ethyl, isopropyl, n-butyl, isobutyl, and t-butyl.

5. The pharmaceutical composition of claim 3, wherein each $R^1$ is methyl.

6. The pharmaceutical composition of claim 3, wherein each $P_i$ is independently selected from adenine, cytosine, guanine, uracil, and thymine.

7. The pharmaceutical composition of claim 1, wherein the pharmaceutical composition is formulated for intravenous administration.

8. The pharmaceutical composition of claim 1, wherein the oligomer is of a formula:

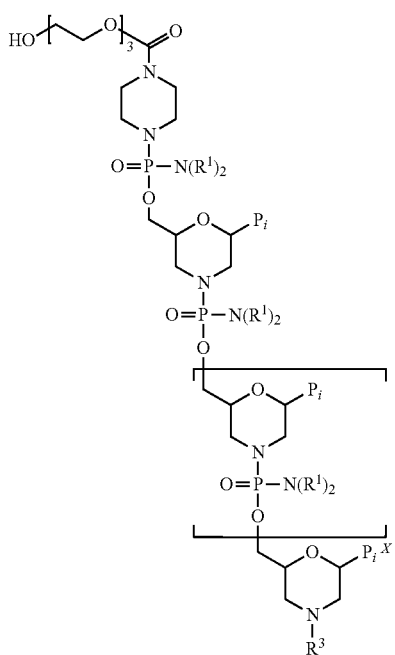

or a pharmaceutically acceptable salt thereof,
wherein:
each $R^1$ is independently a C1-C6 alkyl;
each $P_i$ is independently a purine or pyrimidine base-pairing moiety;
X is an integer from 6 to 38; and
$R^3$ is H.

9. The pharmaceutical composition of claim 8, wherein each $R^1$ is independently selected from methyl, ethyl, isopropyl, n-butyl, isobutyl, and t-butyl.

10. The pharmaceutical composition of claim 8, wherein each $R^1$ is methyl.

11. The pharmaceutical composition of claim 8, wherein each $P_i$ is independently selected from adenine, cytosine, guanine, uracil, and thymine.

12. A pharmaceutical composition comprising a compound of formula:

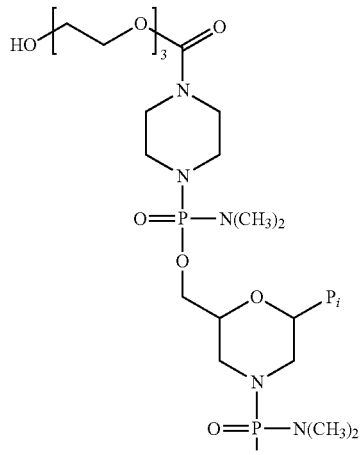

-continued

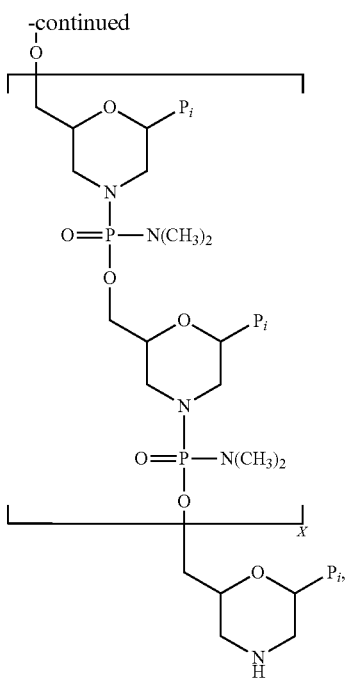

or a pharmaceutically acceptable salt thereof, wherein X is an integer from 3 to 19, and each $P_i$ is independently a purine or pyrimidine base-pairing moiety selected from adenine, cytosine, guanine, uracil, and thymine, and a pharmaceutically acceptable carrier.

13. A pharmaceutical composition comprising a compound of formula:

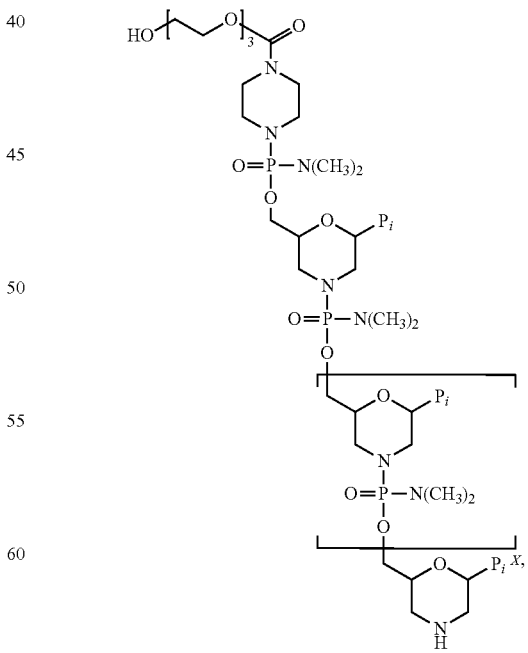

or a pharmaceutically acceptable salt thereof, wherein X is an integer from 6 to 38, and each $P_i$ is independently a purine or pyrimidine base-pairing moiety selected from adenine, cytosine, guanine, uracil, and thymine, and a pharmaceutically acceptable carrier.

\* \* \* \* \*

SEQUENCE LISTING

<160> NUMBER OF SEQ ID NOS: 54

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 1
ctgtgcttac cgggttttcc acctccc                                         27

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 2
atcgtcgtga ctgtctgttg gaggg                                           25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 3
gctcacgttg aggggcatcg                                                 20

<210> SEQ ID NO 4
<211> LENGTH: 20
<212> TYPE: DNA
<213> ORGANISM: Artificial Sequence
<220> FEATURE:

```
<223> OTHER INFORMATION: Description of Artificial Sequence: Synthetic
      antisense oligonucleotide

<400> SEQUENCE: 4
ggtcactcac cggtagagaa                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 5
gggttccaag tctataaagg                                                    20

<210> SEQ ID NO 6
<211> LENGTH: 14
<212> TYPE: DNA
<213> ORGANISM: Homo sapiens

<400> SEQUENCE: 6
tgtgtctttt ccag                                                          14

<210> SEQ ID NO 7
<211> LENGTH: 23
<212> TYPE: DNA
<213> ORGANISM: Homo sapiens

<400> SEQUENCE: 7
tttggagact gccagggacc atg                                                23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 8
catggtccct ggcagtctcc                                                    20

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 9
tcaatgggca aaacatggtc cctggcagtc tccaaa                                  36

<210> SEQ ID NO 10
<211> LENGTH: 15
<212> TYPE: DNA
<213> ORGANISM: Homo sapiens

<400> SEQUENCE: 10
tttgtgttct cccag                                                         15

<210> SEQ ID NO 11
<211> LENGTH: 23
```

<212> TYPE: DNA
<213> ORGANISM: Homo sapiens

<400> SEQUENCE: 11
ggaaacagaa gtacctgtgc gcc                                                23

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 12
ggcgcacagg tacttctg                                                      18

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 13
aatcatttct gctggcgcac aggtacttct gtttcc                                  36

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 14
cccctgcagc acgcgggt                                                      18

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 15
gaggcagggc cggcaggacc ccctgcagca cgcgggt                                 37

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 16
ggcatcgtcg cgggaggctg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic antisense oligonucleotide

<400> SEQUENCE: 17
gggcatcgtc gcgggaggct                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 18
ggggcatcgt cgcgggaggc                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 19
aggggcatcg tcgcgggagg                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 20
gaggggcatc gtcgcgggag                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 21
tgaggggcat cgtcgcggga                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 22
ttgaggggca tcgtcgcggg                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 23
gttgaggggc atcgtcgcgg                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 24
cgttgagggg catcgtcgcg                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 25
acgttgaggg gcatcgtcgc                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 26
aacgttgagg ggcatcgtcg                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 27
taacgttgag gggcatcgtc                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 28
ctaacgttga ggggcatcgt                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 29
gctaacgttg aggggcatcg          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 30
agctaacgtt gagggcatc          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 31
aagctaacgt tgaggggcat          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 32
gaagctaacg ttgaggggca          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 33
tcctcatctt cttgttcctc          20

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 34
aacaacatcg atttcttcct catcttcttg ttcctc          36

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 35
cccggaaggc agtctggc                                                       18

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 36
tcctccatgg cagtgacccg gaaggcagtc tggctg                                   36

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 37
ctactggccg ctgaagggc                                                      19

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 38
gctcaaagtc agatgctact ggccgctgaa gggctt                                   36

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 39
tcgtcggtct ctccgcttct tcttgcc                                             27

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 40
ctctggtggt gggtaagggt                                                     20

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 41
cgggtctgtc gggttccctc tgtggtggg taagggt                                37

<210> SEQ ID NO 42
<211> LENGTH: 30
<212> TYPE: RNA
<213> ORGANISM: Rattus norvegicus

<400> SEQUENCE: 42
ggggcaucgu cgugacuguc uguuggaggg                                30

<210> SEQ ID NO 43
<211> LENGTH: 22
<212> TYPE: RNA
<213> ORGANISM: Rattus norvegicus

<400> SEQUENCE: 43
cgucgugacu gucuguugga gg                                22

<210> SEQ ID NO 44
<211> LENGTH: 22
<212> TYPE: DNA
<213> ORGANISM: Rattus norvegicus

<400> SEQUENCE: 44
cgtcgtgact gtctgttgga gg                                22

<210> SEQ ID NO 45
<211> LENGTH: 28
<212> TYPE: RNA
<213> ORGANISM: Homo sapiens

<400> SEQUENCE: 45
ggcaucgucg cgggaggcug cuggagcg                                28

<210> SEQ ID NO 46
<211> LENGTH: 28
<212> TYPE: RNA
<213> ORGANISM: Rattus norvegicus

<400> SEQUENCE: 46
ccgcgacaua ggacggagag cagagccc                                28

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      scrambled oligonucleotide version of SEQ ID NO: 25

<400> SEQUENCE: 47
actgtgaggg cgatcgctgc                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide (SEQ ID NO: 25 with three mismatched
      Nucleotides)

<400> SEQUENCE: 48
acgatgagtg gcatagtcgc                                20

```
<210> SEQ ID NO 49
<211> LENGTH: 20
<212> TYPE: DNA
<213> ORGANISM: Rattus norvegicus

<400> SEQUENCE: 49
ctccgcaatg ctgaaaggtg                                                    20

<210> SEQ ID NO 50
<211> LENGTH: 24
<212> TYPE: RNA
<213> ORGANISM: Rattus norvegicus

<400> SEQUENCE: 50
ggcgugccuc aaacauggug gcgg                                               24

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgggcacttt gcactgaaac ttacaacacc                                         30

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtcgcagat gaaactctgg tt                                                 22

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctccttgcag ctgcttagac gctgg                                              25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gaagggtgtg accgcaacgt aggag                                              25
```